US011083532B2

United States Patent
Liao

(10) Patent No.: US 11,083,532 B2
(45) Date of Patent: Aug. 10, 2021

(54) MASTER-TO-SLAVE ORIENTATION MAPPING WHEN MISALIGNED

(71) Applicant: INTUITIVE SURGICAL OPERATIONS, INC., Sunnyvale, CA (US)

(72) Inventor: Hsien-Hsin Liao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/693,119

(22) Filed: Nov. 22, 2019

(65) Prior Publication Data

US 2020/0085522 A1 Mar. 19, 2020

Related U.S. Application Data

(63) Continuation of application No. 15/564,160, filed as application No. PCT/US2016/036863 on Jun. 10, 2016, now Pat. No. 10,524,871.

(Continued)

(51) Int. Cl.
*G05B 19/418* (2006.01)
*A61B 34/37* (2016.01)
(Continued)

(52) U.S. Cl.
CPC .............. *A61B 34/37* (2016.02); *A61B 34/35* (2016.02); *A61B 90/361* (2016.02);
(Continued)

(58) Field of Classification Search
CPC .... A61B 2017/00725; A61B 2034/301; A61B 2034/742; A61B 2090/367; A61B 34/35;
(Continued)

(56) References Cited

U.S. PATENT DOCUMENTS 7,333,642 B2 * 2/2008 Green .................. H04N 13/398
382/128
10,524,871 B2 1/2020 Liao
(Continued)

FOREIGN PATENT DOCUMENTS

CN 103097086 A 5/2013
DE 102013110847 B3 1/2015
(Continued)

OTHER PUBLICATIONS

Extended European Search Report for Application No. EP16808359, dated Dec. 10, 2018, 10 pages.
(Continued)

*Primary Examiner* — Harry Y Oh
(74) *Attorney, Agent, or Firm* — Artegis Law Group, LLP

(57) ABSTRACT

A system includes a master manipulator and a controller. The controller determines, before the system enters a following mode, a relative orientation between an orientations of an axis of the master manipulator in an eye frame and a corresponding axis of a slave instrument tip in a camera frame. After the system enters the following mode, the controller determines whether an orientation misalignment between the orientations of the axis of the master manipulator and the corresponding axis of the slave instrument tip is less than or equal to a maximum permitted orientation error. When the orientation misalignment is less than or equal to the maximum permitted orientation error, the controller receives a command indicating a desired orientation of the slave instrument tip from the master manipulator and commands the system to orient the slave instrument tip based on the desired orientation of the slave instrument tip and the relative orientation.

20 Claims, 7 Drawing Sheets

Related U.S. Application Data

(60) Provisional application No. 62/173,844, filed on Jun. 10, 2015.

(51) Int. Cl.

| | | |
|---|---|---|
| *A61B 90/00* | (2016.01) | |
| *B25J 9/16* | (2006.01) | |
| *A61B 34/35* | (2016.01) | |
| *A61B 17/00* | (2006.01) | |
| *A61B 34/00* | (2016.01) | |
| *A61B 34/30* | (2016.01) | |

(52) U.S. Cl.
CPC ........... *B25J 9/1612* (2013.01); *B25J 9/1689* (2013.01); *A61B 2017/00725* (2013.01); *A61B 2034/301* (2016.02); *A61B 2034/742* (2016.02); *A61B 2090/367* (2016.02); *G05B 2219/40405* (2013.01); *G05B 2219/45117* (2013.01); *G05B 2219/45123* (2013.01)

(58) Field of Classification Search
CPC ...... A61B 34/37; A61B 90/361; B25J 9/1612; B25J 9/1689; G05B 2219/40405; G05B 2219/45117; G05B 2219/45123
See application file for complete search history.

(56) References Cited

U.S. PATENT DOCUMENTS

| | | | | |
|---|---|---|---|---|
| 2002/0055795 | A1* | 5/2002 | Niemeyer | B25J 9/1692 |
| | | | | 700/90 |
| 2002/0120252 | A1 | 8/2002 | Brock et al. | |
| 2003/0055410 | A1* | 3/2003 | Evans | A61B 34/32 |
| | | | | 606/1 |
| 2003/0114962 | A1* | 6/2003 | Niemeyer | A61B 1/00149 |
| | | | | 700/245 |
| 2006/0106493 | A1* | 5/2006 | Niemeyer | A61B 34/30 |
| | | | | 700/245 |
| 2007/0142825 | A1* | 6/2007 | Prisco | A61B 34/35 |
| | | | | 606/1 |
| 2009/0062813 | A1* | 3/2009 | Prisco | A61B 34/37 |
| | | | | 606/130 |
| 2009/0171371 | A1* | 7/2009 | Nixon | A61B 34/30 |
| | | | | 606/130 |
| 2009/0326556 | A1* | 12/2009 | Diolaiti | A61B 1/00009 |
| | | | | 606/130 |
| 2010/0274087 | A1* | 10/2010 | Diolaiti | A61B 90/37 |
| | | | | 600/118 |
| 2010/0332031 | A1* | 12/2010 | Itkowitz | B25J 9/1689 |
| | | | | 700/245 |
| 2011/0118748 | A1* | 5/2011 | Itkowitz | A61B 34/37 |
| | | | | 606/130 |
| 2012/0290134 | A1* | 11/2012 | Zhao | B25J 9/1689 |
| | | | | 700/259 |
| 2016/0113728 | A1* | 4/2016 | Piron | A61B 5/0062 |
| | | | | 606/130 |
| 2016/0235489 | A1 | 8/2016 | Gombert et al. | |
| 2017/0143429 | A1* | 5/2017 | Richmond | A61B 34/25 |
| 2018/0036088 | A1* | 2/2018 | Kilroy | A61B 34/30 |

FOREIGN PATENT DOCUMENTS

| | | |
|---|---|---|
| EP | 2594372 A1 | 5/2013 |
| WO | WO-9729690 A1 | 8/1997 |
| WO | WO-2011002593 A1 | 1/2011 |
| WO | WO-2011060139 A2 | 5/2011 |
| WO | WO-2012158458 A2 | 11/2012 |
| WO | WO-2015049095 A1 | 4/2015 |

OTHER PUBLICATIONS

International Search Report and Written Opinion for Application No. PCT/US16/36863, dated Oct. 12, 2016, 18 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

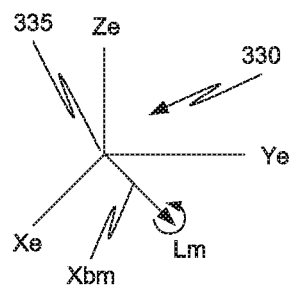
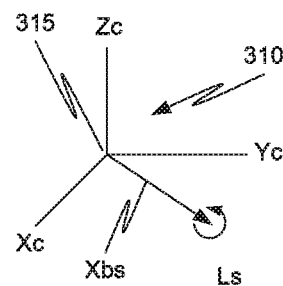
Fig. 5A
Fig. 5B
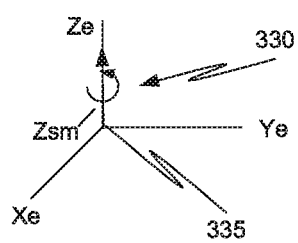
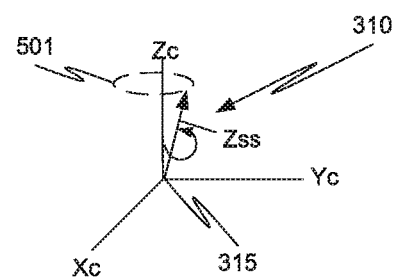
Fig. 5C
(Prior Art)
Fig. 5D
(Prior Art)
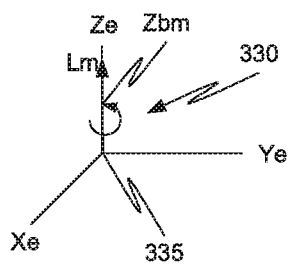
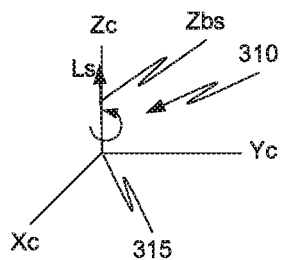
Fig. 5E
Fig. 5F

MASTER-TO-SLAVE ORIENTATION MAPPING WHEN MISALIGNED

RELATED APPLICATIONS

This patent application is a continuation of U.S. patent application Ser. No. 15/564,160, filed Oct. 3, 2017, which is the U.S. national phase of International Patent Application No. PCT/US2016/036863, filed Jun. 10, 2016, which designated the U.S., and which claims priority to and the benefit of the filing date of U.S. Provisional Patent Application 62/173,844, entitled "MASTER-TO-SLAVE ORIENTATION MAPPING WHEN MISALIGNED" filed Jun. 10, 2015, each of which is incorporated herein by reference in its entirety.

BACKGROUND

1. Field of Invention

Aspects of this invention are related to surgical systems, and more particularly are related to controlling orientations of a master tool grip and a slave surgical instrument tip in a surgical system when the two are initially misaligned.

2. Related Art

Surgical systems, such as minimally invasive, teleoperated robotic systems, offer patients many benefits, such as reduced trauma to the body, faster recovery, and a shorter hospital stay. Typically, in a surgical system, a surgeon uses a master tool manipulator, sometimes referred to as a master tool, to control movement of a surgical instrument, referred to as a slave surgical instrument.

In one teleoperated surgical system, a master tool grip of the master tool manipulator is specially designed to be both ergonomic and intuitive for controlling the slave surgical instrument. The surgeon holds the master tool grip in a particular way using his/her forefinger and thumb, so that targeting and grasping involves intuitive pointing and pinching motions.

To enable intuitive control of the slave surgical instrument, the master tool grip is ideally aligned in orientation with the slave surgical instrument tip in a view frame of a stereoscopic viewer in the surgical system. The motions of the slave surgical instrument tip ideally follow master tool motions via teleoperation and are consistent in both directions of motion as well as absolute orientation, i.e., the surgical instrument tip motion follows the motion of the master tool grip. If orientation alignment is not achieved between the master tool and the slave surgical instrument tip, the slave surgical instrument tip neither points in the same absolute direction nor rolls along the same axis as the surgeon is pointing with the master tool.

In one aspect, the master tool manipulator uses motors in a gimbal assembly to actively align the orientation axes of the master tool grip in surgeon eye-view coordinates with the associated slave surgical instrument tip in camera view coordinates. This alignment happens automatically before following is engaged between motion of the master tool and motion of the slave surgical instrument.

Specifically, before entering following on the prior teleoperated surgical system, the system tries to align the orientation of the slave surgical instrument tip in a camera frame with the orientation of the master tool grip in an eye-view frame, sometimes referred to as an eye frame. Typically, the teleoperated surgical system performs a master-slave alignment whenever the system transitions from a mode where the orientation alignment between the master tool grip and the slave surgical instrument tip may have been compromised (after a tool change, camera clutch, slave clutch, swapping of arms in a four arm system, etc.).

In the master-slave alignment process, a set of master wrist joint angles are calculated that cause the orientation of the master tool grip in the eye-view frame to match the orientation of the slave surgical instrument tip in the camera view frame, without changing the master tool grip x-y-z position. The master wrist joints are then commanded to match the calculated angles using the motors.

This should result in alignment of the orientations of the master tool grip and the slave surgical instrument tip. However, if a surgeon grasps the master tool grip too firmly while the motors are positioning the wrist joints in the master tool, there may be both displacement and orientation errors between the master tool grip and the slave surgical instrument tip.

After the wrist joints in the master tool grip are commanded to align the orientations of the master tool grip and the slave surgical instrument tip, the teleoperated surgical system again checks that the master and slave orientations match before allowing the user to enter following. If the orientations don't match, a warning message is displayed and the master-slave alignment is attempted again. This process is repeated until the alignment between the orientations of the master tool grip and the slave surgical instrument tip is within an acceptable tolerance, for example, the orientation misalignment between the master and the slave is smaller than ten degrees.

The orientation misalignment is limited to a small angular deviation so that when the master tool is rotated, the slave surgical tip is typically perceived by the surgeon as rolling in the same way. (See FIGS. 4C and 4D and the related discussion below, which demonstrates that when the orientation misalignment is larger than the allowed small angular deviation, the slave surgical instrument tip rotates in an unexpected way when the master tool grip is rotated.)

When the error in the alignment between the orientations of the master tool grip and the slave surgical instrument tip is smaller than the allowed small orientation misalignment, the master tool grip and the slave surgical instrument tip are considered aligned and the teleoperated surgical system enters following. The requirement to have the master tool grip and the slave surgical instrument tip aligned with such a small orientation misalignment often slows down the surgeon's entry into following.

SUMMARY

A surgical system includes a slave surgical instrument having a slave surgical instrument tip and a master tool manipulator including a master tool grip. The master tool grip is coupled to the slave surgical instrument tip by a controller. The required orientation alignment between the slave surgical instrument tip and the master tool grip is relaxed so that the controller normally enters following where the motion of the slave surgical instrument tip follows the motion of the master tool trip irrespective of any orientation misalignment between the master tool grip and the slave surgical instrument tip.

Thus, the prior art multiple repetitions of the master-slave alignment process to achieve a small orientation misalignment are either eliminated or significantly reduced. Further, despite any swooping orientation misalignment between the master tool grip and the slave surgical instrument tip just before entering following, the motion of the slave surgical instrument tip intuitively follows the motion of the master tool grip and there is no unexpected motion associated with rotation of the master tool grip during following.

In one aspect, the controller is configured to receive a first command from the master tool manipulator and to send a second command including a desired orientation of the slave surgical instrument tip to the slave surgical instrument. The controller is further configured to generate the desired orientation of the slave surgical instrument tip using an orientation of the master tool grip. The orientation of the master tool grip is included in the first command.

The desired orientation of the slave surgical instrument tip generated by the controller preserves a same perceived rotation between the master tool grip and the slave surgical instrument tip even when there is a swooping orientation misalignment between the master tool grip and slave surgical instrument tip. Here, a same perceived rotation means that if the rotation of the master tool grip is perceived as being about a body-fixed axis of the master tool grip, the rotation of the slave surgical instrument is perceived as being about a corresponding body-fixed axis of the slave surgical instrument tip. For example, if the rotation of the master tool grip is perceived as being about the body-fixed x-axis of the master tool grip, the rotation of the slave surgical instrument is perceived as being about a corresponding body-fixed x-axis of the slave surgical instrument tip, or if the rotation of the master tool grip is perceived as being about the body-fixed y-axis of the master tool grip, the rotation of the slave surgical instrument is perceived as being about a corresponding body-fixed y-axis of the slave surgical instrument tip, or if the rotation of the master tool grip is perceived as being about the body-fixed z-axis of the master tool grip, the rotation of the slave surgical instrument is perceived as being about a corresponding body-fixed z-axis of the slave surgical instrument tip.

This is in contrast to a prior system where rotation of the master about a space-fixed axis in the eye frame results in slave rotation about the same space-fixed axis in the camera frame. When the orientation offset between the master tool grip and the slave surgical instrument tip is permitted to be large when following is entered, a rotation of the master grip about its pointing direction can result in a circular slave surgical instrument tip motion about the master pointing direction projected onto the slave view frame Thus, the master tool grip and the slave surgical instrument tip, in the prior system, did not have the same perceived motion for swooping orientation misalignments.

In one aspect, the controller includes a memory and an orientation control module. The memory is configured to store a base orientation of the slave surgical instrument tip in a camera frame and to store a base orientation of the eye frame in the master frame. The controller also is configured to receive a first command from the master tool manipulator. The first command from the master tool manipulator includes a current orientation of the master tool grip in the eye frame. The controller further is configured to send to the slave surgical instrument a second command including the desired orientation of the slave surgical instrument.

It should be appreciated that the controller can be made up of one unit, or multiple different units. When the controller is divided up among different units, the units may be centralized in one location or distributed across the surgical system.

The orientation control module is configured to receive the current orientation of the master tool grip in the eye frame and to generate the desired orientation of the slave surgical instrument. The orientation control module also is configured to retrieve the stored base orientation of the master tool grip and the stored base orientation of the slave surgical instrument tip.

The orientation control module is further configured to generate the desired orientation of the slave surgical instrument tip in the camera frame based on the stored base orientation of the slave surgical instrument tip in the camera frame and a relative rotation matrix. The relative rotation matrix represents a relative rotation of the eye frame in the master frame. The orientation control module compensates for any swooping orientation misalignment between the master tool grip and the slave surgical instrument tip in generating the desired orientation of the slave surgical instrument. Thus, the motion of the slave surgical instrument tip intuitively follows the motion of the master tool grip without any unexpected motion.

Herein, a swooping orientation misalignment is an orientation misalignment which in a prior system would result in the tip of the surgical instrument moving in a perceivable circle about an axis of the surgical instrument tip when the master tool grip was rotated about a corresponding axis of the master tool grip. The prior system is characterized by defining the desired orientation of the slave surgical instrument tip as a product of the current orientation of the master tool grip, a base orientation of the slave surgical instrument tip in the camera reference frame, and a transpose of the base orientation of the master tool grip in the eye frame.

In one aspect, the relative rotation matrix is a combination of the current orientation of the master tool grip in the eye frame and the stored orientation of the eye frame in the master frame.

The controller also includes a master-slave alignment module. The master-slave alignment module is configured to send a command to the master tool to move the master tool grip to align the orientation of the master tool grip in the eye frame with the orientation of the slave surgical instrument tip in the camera frame. Also, after the master tool moves the master tool grip, the master-slave alignment module is configured to determine an orientation alignment error between the orientation of the master tool grip in the eye frame and the orientation of the slave surgical instrument tip in the camera frame. Further, the master-slave alignment module is configured to determine whether the orientation alignment error is smaller than or equal to a maximum permitted swooping orientation misalignment. In one aspect, the maximum permitted swooping orientation misalignment is limited so there is no confusion about which axis a rotation is about, e.g., so that pitch and yaw are not confused. As an example, the maximum permitted swooping orientation misalignment is fifty degrees in one aspect.

In one aspect, the master-slave alignment module is further configured to repeat the sending the command, determining the orientation alignment error, and determining whether the orientation alignment error is smaller than a maximum permitted swooping orientation misalignment only if the orientation alignment error is larger than the maximum permitted swooping orientation alignment error. Here, the maximum permitted swooping orientation alignment error is a different way of saying the maximum permitted swooping orientation misalignment.

In one aspect, the controller also includes a storage module coupled to the master-slave alignment module. The storage module is configured to receive the orientation of the master tool grip in the eye frame and the orientation of the slave surgical instrument tip in the camera frame after the master tool moves the master tool grip if the orientation alignment error is smaller than a maximum large alignment error. The storage module is also configured to store, in a memory, the orientation of the master tool grip in the eye frame as a base orientation of the eye frame in the master frame and to store the orientation of the slave surgical instrument tip in the camera reference as a base orientation of the slave surgical instrument tip in the camera reference.

In one aspect, the surgical system includes an endoscope having a distal end. The camera frame is defined with respect to the distal end of the endoscope. The surgical system also includes a surgeon's console including a viewer and the master tool manipulator.

The method for controlling alignment of a slave surgical instrument tip of a slave surgical instrument in a surgical system with alignment of a master tool grip of a master tool manipulator in the surgical system includes generating, by a controller, a desired orientation of the slave surgical instrument tip using an orientation in an eye frame, the desired orientation of the slave surgical instrument tip preserving a same perceived rotation between the master tool grip and the slave surgical instrument tip with a swooping orientation misalignment between the master tool grip and slave surgical instrument tip.

In one aspect, the generating includes generating, by the controller, a desired orientation of the slave surgical instrument tip in a camera frame based on a rotation offset and a current orientation of the master tool grip in an eye frame, the rotation offset being a combination of a stored orientation of the slave surgical instrument tip in the camera frame and a stored orientation of the eye frame in the master frame. The method also includes sending, by the controller to the slave surgical instrument, a command including the desired orientation of the slave surgical instrument tip, and moving, by the slave surgical instrument in response to the command, the slave surgical instrument tip to the desired orientation.

In one aspect, prior to the generating, the method sends a command to the master tool manipulator to move the master tool grip to align the orientation of the master tool grip in the eye frame with the orientation of the slave surgical instrument tip in the camera frame. After the master tool manipulator moves the master tool grip, the method determines an orientation alignment error between the orientation of the master tool grip in the eye frame and the orientation of the slave surgical instrument tip in the camera frame. The method then determines whether the orientation alignment error is smaller than or equal to a maximum permitted swooping orientation misalignment.

In another aspect, a computer-assisted medical system includes a master tool grip, a slave surgical instrument tip, a controller, and a memory. A roll axis of a master frame is defined along a length of the master tool grip. The master frame is associated with an orientation of the master tool grip, and the master frame is a body-fixed master frame.

A roll axis of a slave frame is defined along a length of the slave surgical instrument tip. The slave frame is associated with an orientation of the slave surgical instrument tip, and the slave frame is a body-fixed slave frame;

The memory contains non-transitory instructions that direct the controller to perform acts including receiving an input corresponding to roll of the master tool grip, generating, in response to the input a command to roll the slave surgical instrument tip, the command being to rotate the slave surgical instrument tip around the roll axis of the body-fixed slave frame without rotating the slave surgical instrument tip around any axis orthogonal to the roll axis of the body-fixed slave frame, and in response to the command, rolling the slave surgical instrument tip around the roll axis of the body-fixed slave frame.

A method for a state of a computer-assisted medical system in which an orientation misalignment exists between the roll axis of a master frame in an eye frame and a roll axis of a slave frame in a camera frame, the master frame being associated with a master tool grip of a master manipulator, the slave frame being associated with a slave surgical instrument tip, the roll axis of the master tool grip being defined along a length of the master tool grip, the roll axis of the slave surgical instrument tip being defined along a length of the slave surgical instrument tip, the method includes receiving an input corresponding to roll of the master tool grip around a roll axis of the master frame, the master frame being a body-fixed master frame. Generating, in response to the input, a command to roll the slave surgical instrument tip, the command being to rotate the slave surgical instrument tip around a roll axis of a body-fixed slave frame without rotating the slave surgical instrument tip around any axis orthogonal to the roll axis of the body-fixed slave frame, and in response to the command, rolling the slave surgical instrument tip around the roll axis of the body-fixed slave frame.

BRIEF DESCRIPTION OF THE DRAWINGS

FIGS. 5A, 5B, 5E, and 5F illustrate that the processes performed by the controller of FIG. 1 to control the master and slave when there is a misalignment overcome the limitations of the prior system.

FIGS. 5C and 5D illustrate an orientation misalignment between the master tool grip and the slave surgical instrument tip that results in the slave surgical instrument tip failing to replicate the perceived motion of the master tool grip when space-fixed frames are utilized.

Figure 1:
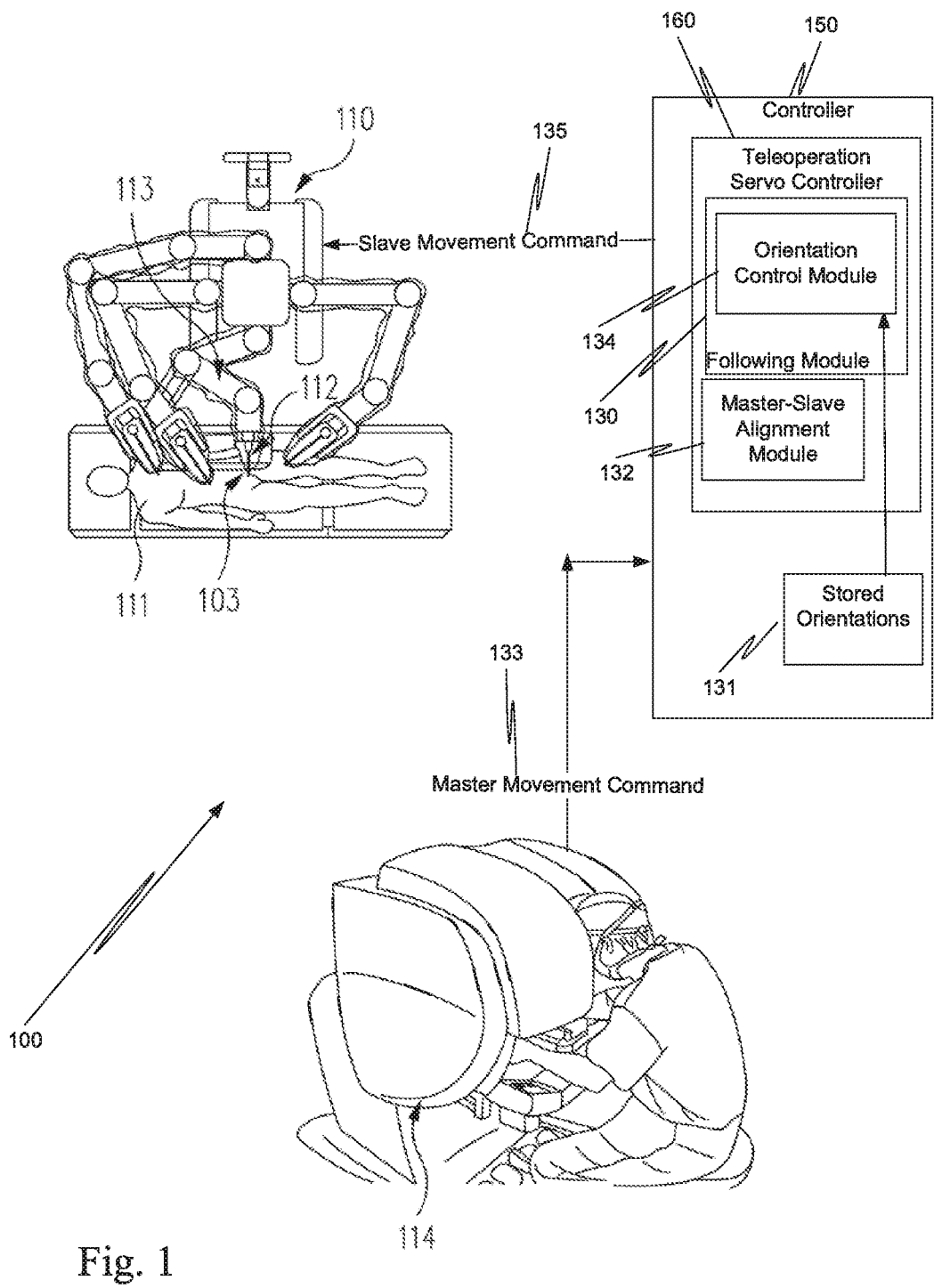
FIG. 1 is a diagrammatic view of a surgical system, which includes a teleoperation servo controller with a following module that includes an orientation control module.

In the drawings, the first digit of a figure number indicates the figure in which the element with that figure number first appears.

DETAILED DESCRIPTION

Aspects of this invention anticipate that the prior art master-slave alignment process for a master tool grip and a slave surgical instrument tip in a teleoperated surgical system 100, sometimes referred to a system 100, may result in a swooping orientation alignment error, i.e., a large misalignment, between the master tool grip and the slave surgical instrument tip ("slave surgical instrument tip" is an example of a "slave instrument tip). To avoid the prior art delays associated with repeating the master-slave alignment process until the orientations of the master tool grip and the slave surgical instrument tip are aligned, controller 150 relaxes the criterion for an acceptable alignment error between the orientations of the master tool grip and the slave surgical instrument tip before following can be entered, i.e., a swooping orientation alignment error is acceptable. The relaxed criterion for an acceptable alignment error between the orientations of the master tool grip and the slave surgical instrument tip before following can be entered reduces the number of required iterations of the master-slave alignment process before following can be entered compared to the prior art process that required a more precise alignment between the orientations of the master tool grip and the slave surgical instrument tip.

Herein, a swooping orientation misalignment is an orientation misalignment where in the above described prior system, a rotation of the master tool grip about its pointing direction would result in a circular slave surgical instrument tip rotation about the master tool grip pointing direction projected on the slave view frame. The prior system is characterized by defining the desired orientation of the slave surgical instrument tip as a product of the current orientation of the master tool grip, a base orientation of the slave surgical instrument tip in the camera reference frame, and a transpose of the base orientation of the master tool grip in the eye frame.

Since the prior system limited the orientation error between the slave surgical instrument tip and the master tool grip to a small orientation error, the circular motion of the slave surgical instrument tip was not perceivable to the user, and so for small orientation errors in the prior system, the slave surgical instrument tip and the master tool grip had the same perceived motion. However, when the requirement for the small orientation error is relaxed, the perceived motion of the slave surgical instrument tip and the master tool grip is no longer the same.

As explained more completely below, controller 150 stores base orientations of the master tool grip and the slave surgical instrument tip upon completion of the master-slave alignment process, and enters following. As used herein "following" is a state of teleoperated surgical system 100 where moving a master tool grip of a master tool in surgeon's console 114 (an example of a console 114) by a user of system 100 results in controller 150 sending a command to a tool 112 (examples including "surgical tool 112" and slave surgical instrument 112") to move the slave surgical instrument tip in the same way as the master tool grip moved. Thus, during following, the movement of the slave surgical instrument tip follows the movement of the master tool grip irrespective of the orientation misalignment between the master tool grip and the slave surgical instrument tip when following was started.

During following each commanded movement of the slave surgical instrument tip from the master tool manipulator is rotated by controller 150 in a particular way, as described more completely below, to compensate for any alignment error between the master tool grip and the slave surgical instrument tip before following was entered. The result of this rotation is that the motion of the slave surgical instrument tip intuitively corresponds to the motion of the master tool grip despite the initial orientation misalignment between the master tool grip and the slave surgical instrument tip. The motion of the slave surgical instrument tip is what expected by the user based on the movement of the master tool grip because the motion of the master tool grip perceived by a user of system 100 is the same as the motion of the slave surgical instrument perceived by the user, i.e., the master tool grip and the slave surgical instrument tip have the same perceived motion.

This is in contrast to prior systems where in some situations, as described more completely below with respect to FIGS. 4A to 4D, a large initial misalignment resulted in unexpected motion of the surgical instrument tip when following the motion of the master tool grip. Specifically, the perceived motion of the master tool grip and the slave surgical instrument tip were different, because rotation of the master tool grip about a space-fixed axis in the eye frame resulted in slave surgical instrument tip rotation about the same space-fixed axis in the camera frame. When the orientation offset between the master tool grip and the slave surgical instrument tip is permitted to be large when following is entered, a rotation of the master tool grip about its pointing direction can result in a circular slave surgical instrument tip motion about the master pointing direction projected onto the slave view frame. See FIGS. 4C and 4D and the accompanying description below.

More specifically, in one aspect, controller 150 (FIG. 1) is configured to receive a first command 133 from the master tool manipulator (not shown, but see master tool manipulator 370 (FIG. 3C)), and to send a second command 135 including a desired orientation of the slave surgical instrument tip to slave surgical instrument 112. Controller 150 is configured to generate the desired orientation of the slave surgical instrument tip using an orientation of the master tool grip. The orientation of the master tool grip is included in first command 133. Herein, "second command 135" is sometimes referred to as "control command 135." Herein, a "master movement command 133" is an example of first command 133, and "slave movement command 135" is an example of second command 135.

The desired orientation of the slave surgical instrument tip generated by controller 150 preserves a same perceived rotation between the master tool grip and the slave surgical instrument tip even when there is a swooping orientation misalignment between the master tool grip and slave surgical instrument. Here, a same perceived rotation means that if the rotation of the master tool grip is perceived as being about a body-fixed axis of the master tool grip, the rotation of the slave surgical instrument is perceived as being about a corresponding body-fixed axis of the slave surgical instrument tip. For example, if the rotation of the master tool grip is perceived as being about the body-fixed x-axis of the master tool grip, the rotation of the slave surgical instrument is perceived as being about a corresponding body-fixed x-axis of the slave surgical instrument tip, or if the rotation of the master tool grip is perceived as being about the body-fixed y-axis of the master tool grip, the rotation of the slave surgical instrument is perceived as being about a corresponding body-fixed y-axis of the slave surgical instrument tip, or if the rotation of the master tool grip is perceived as being about the body-fixed z-axis of the master tool grip, the rotation of the slave surgical instrument is perceived as being about a corresponding body-fixed z-axis of the slave surgical instrument tip.

As just explained, this is in contrast to a prior system where when the orientation offset is permitted to be large, a rotation of the master tool grip about its pointing direction can result in a circular slave surgical instrument tip motion about the master pointing direction projected onto the slave view frame. Thus, the master tool grip and the slave surgical instrument tip, in the prior system, did not have the same perceived motion for swooping orientation errors.

In surgical system 100, a user, typically a surgeon, sits at a console 114 and grasps a master tool grip (not shown)

between the thumb and forefinger so that targeting and grasping involves intuitive pointing and pinching motions. The master tool grip is part of a master tool manipulator, sometimes called a master tool. The motion of the master tool grip is used by controller 150, as described more completely below, to move a tip of slave surgical instrument 112, e.g., move an end effector of a surgical instrument.

Console 114 (FIGS. 1 and 2A) includes a master display, sometimes referred to as a viewer, which displays at least a stereoscopic image 210 (FIG. 2A) of a surgical site 103 of patient 111. Stereoscopic image 210 typically includes an image 203 of surgical site 103, an image 212 of a part of slave surgical instrument 112, and an image 212T of a tip of slave surgical instrument 112. Console 114 also includes one or more foot pedals (not shown).

Console 114 (FIG. 1) is connected to a controller 150 that is turn is connected to a cart 110, which supports a plurality of robotic arms that includes robotic arm 113. Slave surgical instrument 112 is held and positioned by robotic arm 113. While it is not shown in FIG. 1, an endoscope, held by another of the robotic arms, is typically used to provide stereoscopic image 210.

Figure 2A:
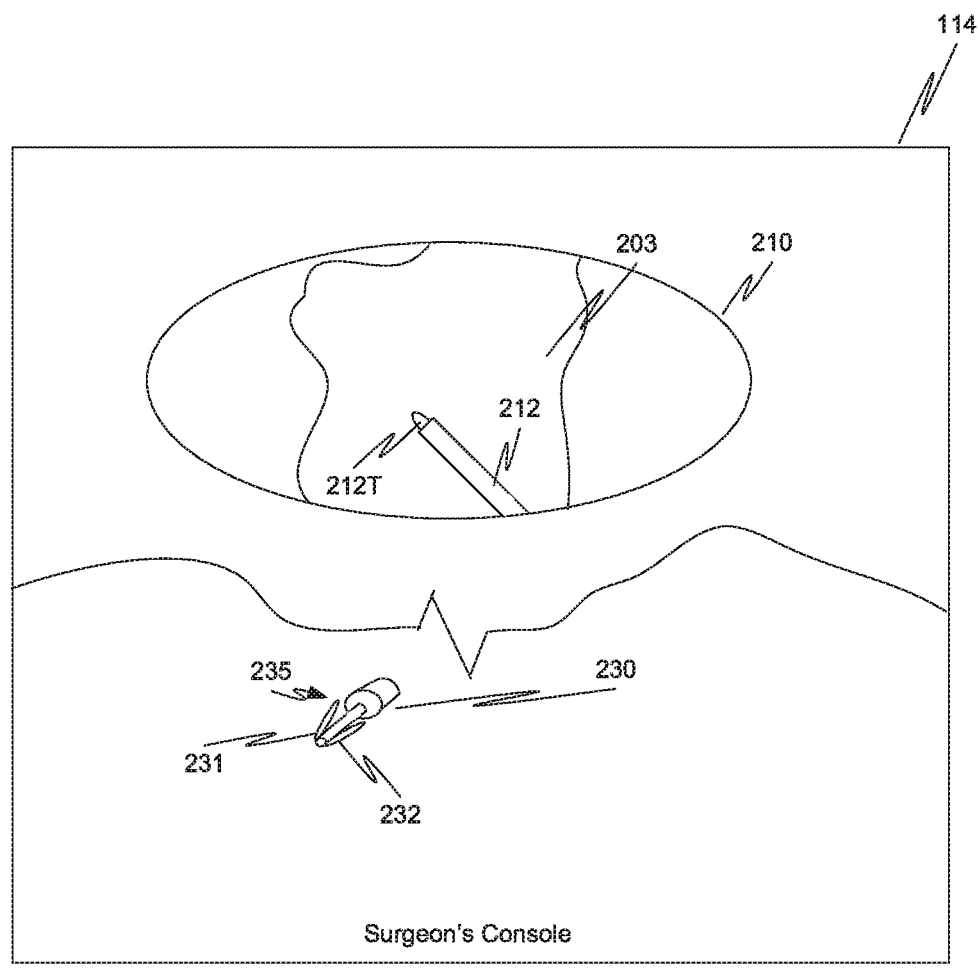
FIG. 2A is diagrammatic view of parts of the surgeon's console of FIG. 1.

The surgeon sits comfortably and looks into the master display on console 114 throughout surgery. The surgeon performs a medical procedure by manipulating at least master tool grip 230 (FIG. 2A). Master tool grip 230 includes two levers 231, 232, sometimes called pinchers, which the surgeon typically grasps between the thumb and forefinger. The master tool provides a master movement command 133 including at least a current orientation of master tool grip 230. Master movement command 133 is sometimes referred to as a first command.

In response to master movement command 133 from master tool, controller 150, e.g., teleoperation servo controller 160 of controller 150, sends a slave movement command 135 to slave surgical instrument 112. In response to slave movement command 135, slave surgical instrument 112 positions a tip of slave surgical instrument 112 as directed in slave movement command 135. Slave movement command 135 is sometimes referred to as a second command.

Typically, console 114 includes at least two master tools and each master tool controls a different surgical instrument. Herein a single master tool with master tool grip 230 is considered. In view of this description, the aspects of this invention can be implemented for any desired number of master tools.

The master display is positioned in console 114 (FIG. 1) near the surgeon's hands so that image 210 (FIG. 2A), which is seen in the master display, is oriented so that the surgeon feels that she or he is actually looking directly down onto surgical site 103. Image 212 of tool 112 appears to be located substantially where the surgeon's hands are located and oriented substantially as the surgeon would expect tool 112 to be based on the position of her/his hand. However, typically, the surgeon cannot see the position or orientation of master tool grip 230 while viewing image 210.

The real-time image from the endoscope is projected into perspective image 210 (e.g., a stereoscopic image 210) such that the surgeon can manipulate a surgical instrument end effector of tool 112, through its associated master tool grip 230, as if viewing the workspace in substantially true presence. By true presence, it is meant that the presentation of an image is a true perspective image simulating the viewpoint of an operator that is physically manipulating the surgical instrument. Thus, controller 150 transforms the coordinates of tool 112 to a perceived position so that the perspective image is the image that the surgeon would see if the endoscope were looking directly at tool 112 from the surgeon's eye-level during an open cavity procedure.

Controller 150 performs various functions in system 100. Controller 150 receives the images from an endoscope and generates the stereoscopic image that the surgeon sees. Controller 150 uses teleoperation servo controller 160 to transfer the mechanical motion of master tool grip 230 to an associated slave surgical instrument through slave movement commands 135, so that the surgeon can effectively manipulate tool 112. Controller 150 and teleoperation servo controller 160 are similar to prior systems with the exception of the aspects described more completely below.

Although described as a controller 150, it is to be appreciated that controller 150 may be implemented in practice by any number of modules and each module may include any combination of components. Each module and each component may include hardware, software that is executed on a processor, and firmware, or any combination of the three. Also, the functions and acts of controller 150, as described herein, may be performed by one module, or divided up among different modules or even among different components of a module. When divided up among different modules or components, the modules or components may be centralized in one location or distributed across system 100 for distributed processing purposes. Thus, controller 150 should not be interpreted as requiring a single physical entity as in some aspects controller 150 is distributed across system 100.

The number of surgical instruments used at one time, and consequently, the number of surgical instruments used in system 100 generally depends on the medical procedure being performed and on the space constraints within the operating room, among other factors. If it is necessary to change one or more of the surgical instruments being used during a procedure, an assistant may remove the surgical instrument, and replace the surgical instrument with a different surgical instrument.

When there are only two master tools in system 100, and when the surgeon wants to control movement of a slave surgical instrument different from the two slave surgical instrument coupled to the two master tools, the surgeon may lock one or both of the two slave surgical instruments in place. The surgeon then associates one or both of the master tools with other slave surgical instruments held by other of the robotic arms and then controller 150 becomes active with respect to those surgical instruments.

To facilitate the discussion of the acts performed by controller 150, various frames are used. A frame is a Cartesian coordinate system that includes three spatial axes, e.g., x-, y-, and z-axes, and three orientations, e.g., pitch, yaw, and roll. Each of the orientations is a rotation about one of the spatial axes.

A first frame is referred to as an eye frame. In one aspect, the origin of the eye frame is chosen to correspond with a position where the surgeon's eye is normally located when he or she is viewing surgical site 103 in surgeon's console 114. In master movement command 133, the position and orientation of master tool grip 230 are specified in the eye frame, in one aspect. Techniques for determining the position and orientation of master tool grip 230 in the eye frame are known. See for example, U.S. Pat. No. 6,671,581 B2 (granted 30 Dec. 2003, and disclosing "Camera Referenced Control In a Minimally Invasive Surgical Apparatus"), which is incorporated herein by reference.

A second frame is referred to as a master frame. In one aspect, the origin of the master frame is chosen as a point on master tool grip 230.

A third frame is referred to as a camera frame. In one aspect, the origin of the camera frame is chosen to correspond with a position on the distal end of the endoscope. In slave movement command 135, a desired orientation of the salve surgical instrument tip is specified in the camera frame, in one aspect. Techniques for determining the position and orientation of slave surgical instrument tip in the camera frame are known. See for example, U.S. Pat. No. 6,671,581 B2, which was previously incorporated by reference.

A fourth frame is referred to as a slave frame. In one aspect, the origin of the slave frame is chosen as a point on the slave surgical instrument tip.

Figure 2B:
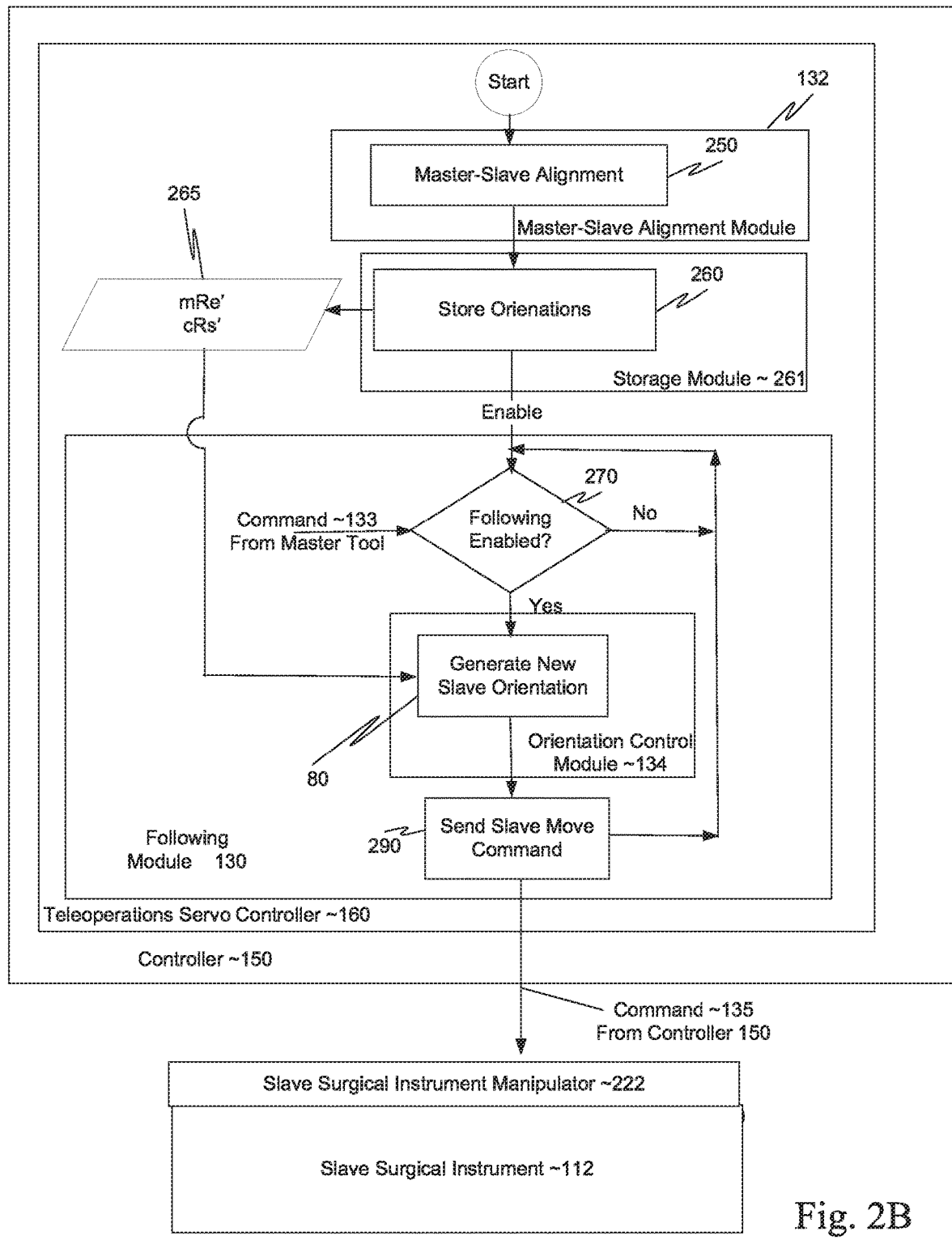
FIG. 2B is a process flow diagram that illustrates processes implemented by the controller of FIG. 1, in one aspect.

FIG. 2B is a process flow diagram of a following process that uses relative rotation with the alignment of the master tool and the alignment of the slave surgical instrument tip immediately before the following process is started. The following process is implemented by a following module 130 in controller 150.

In this following process, the motion of the slave surgical instrument tip follows the motion of the master tool without any unexpected motion of the slave surgical instrument tip. As described more completely below, a prior following process that also used relative rotation resulted in unexpected rotation of the slave surgical instrument tip when the master tool and the slave surgical instrument tip were misaligned on entering the following process.

In this aspect, a FOLLOWING ENABLED check process 270 (FIG. 2B) determines whether system 100 has enabled following between master tool grip 230 and the slave surgical instrument tip. In one aspect, FOLLOWING ENABLED check process 270 is implemented by following module 130 (FIGS. 1 and 2B). Following module 130 is included in controller 150, and so controller 150 determines whether following is enabled. Similarly, each of the other processes and acts described with respect to the following session of FIG. 2B is performed by teleoperation servo controller 160 of controller 150, and so controller 150 can be said to perform the processes and acts.

If following is enabled, FOLLOWING ENABLED check process 270 passes each master movement command 133 from the master tool manipulator to GENERATE NEW SLAVE ORIENTATION process 280, and otherwise takes no action. FOLLOWING ENABLED check process 270 should not be interpreted as requiring controller 150 to continually poll to determine whether following is enabled. FOLLOWING ENABLED check process 270 is illustrative only that following cannot be initiated until following is enabled. The determination of whether following is enabled could be done for example, by an event handler which launches the following process, when a following enabled event is received.

GENERATE NEW SLAVE ORIENTATION process 280 uses the information in the master tool command and stored orientations 131, e.g., stored orientations mRe' and cRs', to generate a desired orientation cRs_des of the slave surgical instrument tip in a camera frame. Stored orientations mRe' and cRs' are referred as base orientations. GENERATE NEW SLAVE ORIENTATION process 280 is implemented by orientation control module 134 that is included in controller 150.

Master movement command 133 includes an orientation eRm of master tool grip 230 in an eye frame. Orientation eRm is sometimes referred to as a current orientation of the master tool grip in the eye frame.

Orientations mRe' and cRs' are stored in memory 265 before the following process, sometimes referred to as a following session, is started. Herein, a prime notation on an orientation reference numeral signifies that the orientation is a snapshot of the corresponding orientation state the moment before entering following, and, in one aspect, the stored orientation is a fixed quantity that does not change in the same following session.

Stored orientation mRe' is the last orientation of the eye frame in a master frame before the current following session was started. In this aspect, instead of holding the eye frame stationary and considering the movement of the master tool grip as in prior systems, the master tool grip is assumed to remain stationary and the eye frame is moving. This is an alternative technique for representing the motion of the master tool grip.

Stored orientation cRs' is the last orientation of the slave surgical instrument tip in the camera frame before the current following session was started. Orientations mRe' and cRs' are stored before a following session is started, and so are referred to as base orientations, because they are the orientation on which changes in orientation during following session are based, i.e., the new orientation of the slave surgical instrument tip is determined relative to the stored base orientation cRs' of the slave surgical instrument tip.

GENERATE NEW SLAVE ORIENTATION process 280 generates desired orientation cRs_des of the slave surgical instrument tip in the camera frame based on a rotation offset Roffset and current orientation eRm of the master tool grip in the eye frame, e.g., the desired orientation cRs_des of the slave surgical instrument tip in the camera frame is defined as:

$$cRs\_des = Roffset * eRm$$

Rotation offset Roffset is a combination of the stored orientation cRs' of the slave surgical instrument tip in the camera frame and the stored orientation mRe' of the eye frame in the master frame. In one aspect, $$Roffset = cRs'*mRe'$$

Thus, $$cRs\_des = cRs'*mRe'*eRm$$

As previously stated, the last expression desired orientation cRs_des demonstrates that desired orientation cRs_des of the slave surgical instrument tip in the camera frame is a combination of the two stored orientations and the current orientation of the master tool grip in the eye frame. It is further demonstrated below that (mRe'*eRm) is a transpose of a relative rotation matrix R2. Thus, the desired orientation cRs_des of the slave surgical instrument tip in the camera frame is a product of the stored orientation cRs' of the slave surgical instrument tip in the camera frame and a transpose of relative rotation matrix R2. Relative rotation matrix R2 represents a relative rotation of eye frame 330 in master frame 340.

Determining cRs_des of the slave surgical instrument tip in the camera frame using the product of the stored orientation cRs' of the slave surgical instrument tip in the camera frame and a transpose of relative rotation matrix R2 compensates for any orientation alignment error between master tool grip 230 and the surgical instrument tool tip when following is entered. Further, as discussed more completely below, this process does not result in any unexpected motion of the surgical instrument tool tip, and so the motion of the surgical instrument tip is said to intuitively follow the motion of master tool grip 230.

After GENERATE NEW SLAVE ORIENTATION process 280 generates desired orientation cRs_des of the slave surgical instrument tip in the camera frame, SEND SLAVE MOVE COMMAND process 290 sends a slave movement command 135, sometimes referred to as command 135, which includes desired orientation cRs_des to a slave surgical instrument manipulator 222 or other slave instrument controller. In response to command 135, slave surgical instrument manipulator 222 moves the slave surgical instrument tip to the desired orientation. It is known how a slave surgical instrument responds to a command to change the orientation of the instrument tip, and so the change in orientation of the instrument tip by the slave surgical instrument is not considered in further detail. After sending slave movement command 135, SEND SLAVE MOVE COMMAND process 290 returns to FOLLOWING ENABLED check process 270.

The following process of FIG. 2B is entered when system 100 first starts and continues until system 100 disables following. When following is disabled by system 100, in one aspect, an SWOOPING ORIENTATION ERROR ACCEPTABLE check process (not shown, but see process 620 in FIG. 6) in MASTER-SLAVE ALIGNMENT process 250 determines whether an orientation misalignment between the orientation of the master tool grip in the eye frame and the slave surgical instrument tip in the camera frame is smaller than or equal to a maximum permitted swooping orientation misalignment.

If the SWOOPING ORIENTATION ERROR ACCEPTABLE check process determines that orientation misalignment between the orientation of the master tool grip in the eye frame and the slave surgical instrument tip in the camera reference is smaller than or equal to a maximum permitted swooping orientation misalignment, STORE ORIENTATIONS process 260 receives and stores the current orientation of the slave surgical instrument tip in the camera frame, and receives and stores the transpose of the current orientation of the master tool grip in the eye frame, which is the orientation of the eye frame in the master frame. In one aspect, STORE ORIENTATIONS process 260, sometimes referred to as process 260, is implemented by storage module 261. Storage module 261 is included in controller 150. Upon completion of process 260, a following session is enabled.

During the initial start-up of system 100 and when the SWOOPING ORIENTATION ERROR ACCEPTABLE check process determines that the orientation misalignment is greater than the maximum permitted swooping orientation misalignment, MASTER-SLAVE ALIGNMENT process 250 sends a command to the master tool in surgeon's console 114 to move master tool grip 230 so that the orientation of master tool grip 230 in the eye frame matches the orientation of the slave surgical instrument tip in the camera frame. The use of motors in the master tool to change the orientation of master tool grip 230 is known, and so is not considered in further detail. Upon completion of the POSITION MASTER TOOL process (not shown, but see process 610 in FIG. 6), the SWOOPING ORIENTATION ERROR ACCEPTABLE check process is repeated.

The larger allowed misalignment at the end of MASTER-SLAVE ALIGNMENT process 250 means that in most cases, MASTER-SLAVE ALIGNMENT process 250 is performed only once and then following is entered. Thus, any frustration that was previously experienced by the surgeon due to multiple warnings of misalignment is minimized, if not eliminated.

It will be appreciated that controller 150 includes at least one, and typically a plurality, of processors which during a following session determine new corresponding positions and orientations of the slave surgical instrument tip in response to master tool movement input commands on a continual basis determined by the processing cycle rate of the controller 150. A typical processing cycle rate of controller 150 is about 1300 Hz. Thus, when the master tool is moved from one position to a next position, the corresponding desired movement of the slave surgical instrument tip is determined at about 1300 Hz. Of course, controller 150 can have any appropriate processing cycle rate depending on the processor or processors used in the controller.

Figure 3A:
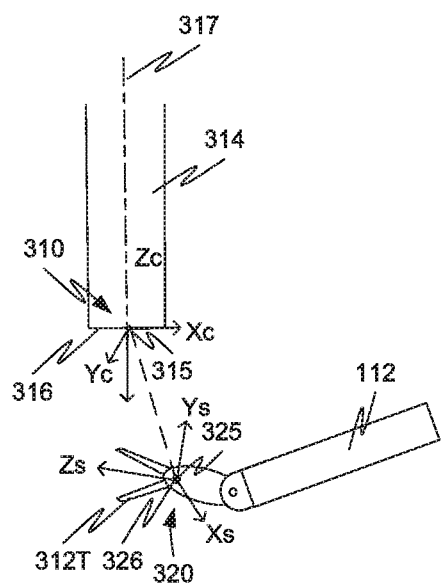
FIGS. 3A to 3C illustrate various frames used by the controller of FIG. 1.
Figure 3C:
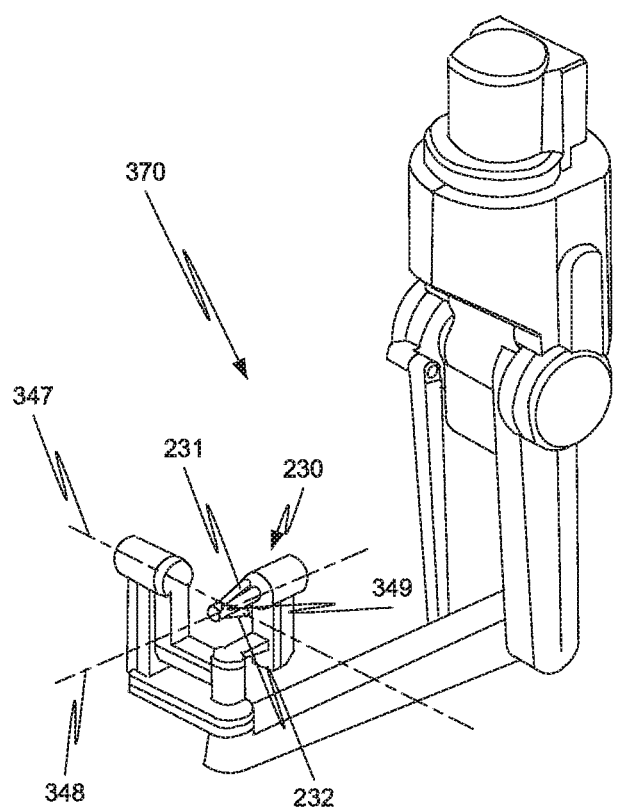
Figure 3B:
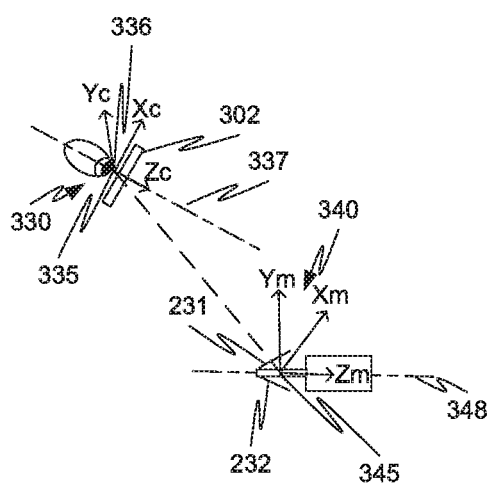

Prior to considering the inventive aspects described above in further detail, specific examples of each of the references frames are presented with respect to FIGS. 3A to 3C. Then, to help illustrate the inventive aspects more clearly, prior systems and their short comings with respect to swooping orientation misalignments are discussed. Finally, the inventive aspects described above are considered in more detail and compared with the prior systems.

In FIG. 3A, a camera frame 310 is positioned such that its origin 315 is positioned at the viewing end 316 of endoscope 314. In this aspect, camera frame 310 is a Cartesian coordinate system, e.g., includes an x-axis Xc, a y-axis Yc, and a z-axis Zc. Rotation about z-axis Zc is referred to roll. Rotation about x-axis Xc is referred to as pitch, and rotation about the y-axis Yc is referred as yaw. Naturally, x-axis Xc, and y-axis Yc, are positioned in a plane perpendicular to z-axis Zc. The association of an orientation with a particular axis is illustrative only and is not intended to be limiting. The association between a particular axis and a rotation can be different than what is described herein, so long as the associations are defined consistently in each of the reference frames.

Conveniently, z-axis Zc of camera frame 310 extends axially along a viewing axis 317 of endoscope 314. While in FIG. 3A, viewing axis 317 is shown in coaxial alignment with a shaft axis of endoscope 314, it is to be appreciated that viewing axis 317 also can have an angle with respect to the lengthwise axis of endoscope 314. Thus, endoscope 314 also can be an angled endoscope. Endoscope 314 is typically angularly displaceable about its lengthwise axis. The x-, y- and z-axes are fixed relative to viewing axis 317 of endoscope 304 so as to displace angularly about the lengthwise axis in sympathy with angular displacement of endoscope 304 about its lengthwise axis.

To enable teleoperation servo controller 160 to determine slave position and orientation, a slave frame 320 is defined on or attached to slave surgical instrument tip 312T. In the example of FIG. 3A, slave frame 320 has its origin 325 at a pivotal connection 326. In this aspect, slave frame 320 is a Cartesian coordinate system, e.g., includes an x-axis Xs, a y-axis Ys, and a z-axis Zs. Rotation about z-axis Zs is referred to roll. Rotation about x-axis Xs is referred to as pitch, and rotation about the y-axis Ys is referred as yaw. Naturally, x-axis Xs, and y-axis Ys, are positioned in a plane perpendicular to z-axis Zs.

Conveniently, one of the axes e.g. z axis Zs, of slave frame 320 is defined to extend along an axis of symmetry, or the like, of instrument tip 312T. The orientation of slave surgical instrument 112 is defined by the orientation of slave frame 320 having its origin at pivotal connection 326 relative to camera frame 310. Similarly, the position of slave surgical instrument 112 is defined by the position of the origin of slave frame 320 relative to origin 315 of camera frame 310.

An origin 335 of eye frame 330 (FIG. 3B) is chosen such that origin 335 corresponds with a position 336 where the surgeon's eye is normally located when he or she is viewing the surgical site at viewer 302 in surgeon's console 114. In this aspect, eye frame 330 is a Cartesian coordinate system, e.g., includes an x-axis Xe, a y-axis Ye, and a z-axis Ze. Rotation about z-axis Ze is referred to roll. Rotation about x-axis Xe is referred to as pitch, and rotation about the y-axis Ye is referred as yaw. Naturally, x-axis Xe, and y-axis Ye are positioned in a plane perpendicular to z-axis Ze.

Z-axis Ze extends along a line of sight of the surgeon, indicated by axis 337, when viewing the surgical site through the viewer 302. Conveniently, y-axis Ye is chosen to extend generally vertically relative to viewer 302, and x-axis Xe is chosen to extend generally horizontally relative to viewer 302.

To enable controller 150 to determine the position and orientation of master tool grip 230 within eye frame 330, a point on master tool grip 230 (FIGS. 3B and 3C) is chosen which defines an origin 345 of a master frame 340. In one aspect, this point is chosen at a point of intersection 349 between a first rotational axis 347 of master tool manipulator 370 and a second rotational axis 348 of master tool manipulator 370. (See also point 3A in FIG. 6A of U.S. Pat. No. 6,671,581 B2).

In this aspect, master frame 340 is a Cartesian coordinate system, e.g., includes an x-axis Xm, a y-axis Ym, and a z-axis Zm. Rotation about z-axis Zm is referred to roll. Rotation about x-axis Xm is referred to as pitch, and rotation about the y-axis Ym is referred as yaw. Naturally, x-axis Xm, and y-axis Ym are positioned in a plane perpendicular to z-axis Zm.

Z-axis Zm of the master frame 340 on master tool grip 230 is chosen to extend along an axis of symmetry of pinchers 231 and 232, which extends coaxially along rotational axis 348. The orientation of master tool grip 230 within eye frame 330 is defined by the orientation of the master frame 340 relative to eye frame 330. The position of master tool grip in eye frame 330 is defined by the position of origin 345 relative to the origin of eye frame 330. Mapping between the master frame and the eye frame is known. See for example, U.S. Pat. No. 6,671,581 B2.

Control between master tool grip movement and slave surgical instrument tip movement is achieved using position ePm and orientation eRm of master tool grip 230 in eye frame 330 and position cPs and orientation cRs of slave surgical instrument tip 312T in camera frame 310. Here, position ePm is a three by one matrix (represented by P in ePm) with the x, y, z position of the origin 345 of master frame 340 (represented by m in ePm) in eye frame 330 (represented by e in ePm). Similarly, position cPs is a three by one matrix (represented by P in cPs) with the x, y, z position of the origin 325 of slave frame 320 (represented by s in cPs) in camera frame 310 (represented by c in cPm). Orientation eRm is a three by three rotation matrix (represented by R in eRm) specifying the orientation of master frame 340 (represented by m in eRm) in eye frame 330 (represented by e in eRm). Similarly, orientation cRs is a three by three rotation matrix (represented by R in cRs) specifying the orientation of slave frame 320 (represented by s in cRs) in camera frame 310 (represented by c in cRm).

A prior system tried to align the master tool grip and the slave surgical instrument, as described above in the BACKGROUND. In this system, the orientation alignment mismatch just prior to entering following was limited to a small orientation misalignment. With respect to processing the orientation, the previous system behavior can be best described as "view-frame centric." Prior to entering following, the prior system stored the orientation eRm' of the master tool grip in the eye frame and stored the orientation cRs' of the slave surgical instrument tip in camera frame. Orientation eRm' and orientation cRs' were stored as rotation matrices.

In the prior system, an offset matrix Roffset_prior was generated from the stored orientations by multiplying the two stored orientations, e.g., by multiplying the rotation matrices, i.e.:

$$\text{Roffset\_prior} = sRc'*eRm'$$

It is known that $sRc = cRs^T$, which means $sRc' = cRs'^T$, and so the rotation offset is $$\text{Roffset\_prior} = sRc'*eRm' = cRs'^T*eRm'$$

In following, the master tool grip undergo additional rotation, which is expressed in eye frame:

$$eRm = R1*eRm'$$

Thus, the current orientation eRm is defined as being equal to the product of a relative master rotation matrix R1 in the eye frame and stored orientation eRm'.

In the prior system, the desired slave orientation cRs_des of the slave surgical instrument tip in the camera frames was defined as:

$$cRs\_des = eRm*\text{Roffset\_prior}^T$$

Substituting the above definition of rotation offset Roffset in the previous expression gives:

$$cRs\_des = eRm*(cRs'^T*eRm')^T$$

Substituting the above definition of additional rotation eRm in the previous expression gives $$cRs\_des = R_1*eRm'*mRe'*cRs'$$

However, it is known that rotation matrices are orthogonal matrices, i.e., $$mRe'*eRm' = I$$

Thus, $$cRs\_des = R1*cRs' \qquad (1)$$

Effectively, to send a movement command to control movement of the slave surgical instrument when the master tool grip was moved, the prior system first computed relative master rotation matrix R1 in the eye frame, e.g., from above, the relative master rotation matrix was defended as $$eRm = R1*eRm'$$

$$eRm*eRm'^T = R1*eRm'*eRm'^T$$

but $$eRm'*eRm'^T = I$$

$$R1 = eRm*eRm'^T$$

To compute relative master rotation matrix R1 in the eye frame, the prior system multiplied the current rotation matrix eRm by the transpose of the stored orientation eRm'.

To obtain desired slave orientation cRs_des, the prior system then applied the same relative master rotation matrix R1 to the snapshot slave orientation cRs' in camera frame 310. This process of determining desired slave orientation cRs_des is called "view-frame centric," because the system monitors the delta of the motion of the master tool grip in the eye frame, and replicates that delta on the slave surgical instrument in the camera frame. The use of motion relative to the misalignment between the master tool grip in the eye frame and the slave surgical instrument tip in the camera frame creates motion that would confuse the user of the prior system if the system allowed a swooping orientation misalignment just prior to entering following.

Figure 4A:
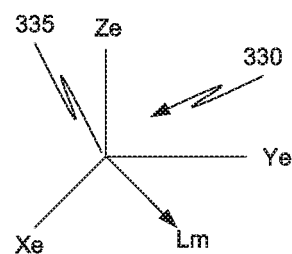
FIGS. 4A to 4D illustrate a problem with a prior systems relative control of orientation when there is misalignment between the master and slave.
Figure 4B:
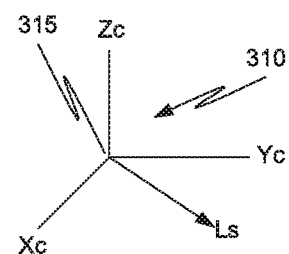

FIG. 4A is a graphic representation of the location Lm of the master tool grip in eye frame 330 following the master-slave alignment in the prior system. For ease of discussion, location Lm is in the Xe-Ye plane. Location Lm is saved as (ePm', eRm'). Location Lm is defined in space with respect to eye frame 330, and so in the prior system, frame 340 is a space-fixed coordinate system. FIG. 4B is a graphic representation of the location Ls of the slave surgical instrument tip in camera frame 310 following the master-slave alignment. Location Ls is in the Xc-Yc plane. Location Ls is saved as (cPs', cRs'). In this example, location Ls is defined in space with respect to camera frame 310, and so in the prior system, frame 320 is a space-fixed coordinate system. At the end of the master-slave alignment, the slave surgical instrument tip misalignment with the master tool grip is larger than that previously allowed by the system.

Figure 4C:
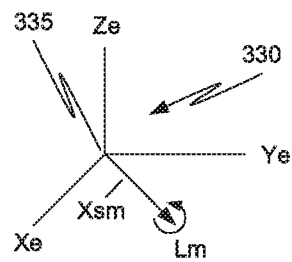

Upon entering following, the surgeon rotates the master tool grip, as illustrated in FIG. 4C. The rotation is about space fixed x-axis Xsm in the Xe-Ye plane. Rotation of the master tool grip about space-fixed axis Xsm in the eye frame results in slave surgical instrument tip rotation about the same space-fixed axis Xss in the camera frame. When the orientation offset is permitted to be large, a rotation of the master tool grip about its pointing direction can result in a circular slave surgical instrument tip motion about the master pointing direction projected onto the slave view frame. However, the surgeon is likely to anticipate that the slave surgical instrument tip will rotate about its x-axis Xss in the Xc-Yc plane.

Figure 4D:
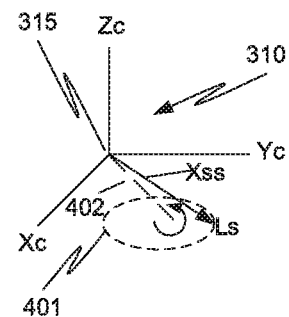

With the swooping orientation misalignment, the prior art system still determines desired slave orientation cRs_des in response to the rotation of the master tool grip as just described. Due to the initial large displacement in orientation, the slave surgical instrument tip does not rotate as expected, because when the relative rotation is applied to the slave surgical instrument tip, the rotation of the slave surgical instrument tip is no longer in the in the Xc-Yc plane. Rather than rotate in the Xc-Yc plane, the slave surgical instrument tip rather rotates along a circular path 401 in camera frame 310. In FIG. 4D, dashed line 402 represents the location of slave surgical instrument tip 312T if master tool grip 230 and slave surgical instrument tip 312T were aligned. If the two were aligned, rotation of master tool grip about one of its axes would result in slave surgical instrument tip rotating about the same one of its axes with no spatial displacement from the axis. However, due to the swooping orientation misalignment, the path of the rotation of slave surgical instrument is displaced from the axis as show by path 401.

Thus, in this example, the perceived motion of rotating the master tool grip in a plane about an axis Xsm of the master tool grip does not result in a perceived motion of the surgical instrument tip rotating about a corresponding axis indicated by dashed line 402 in a plane. Rather, as just described, the movement of the slave surgical instrument tip is along a circular path 401. Circular path 401 is in a plane perpendicular to the Xc-Yc plane. Hence, for swooping orientation misalignments in the prior system, the perceived rotation of the master tool grip and the perceived rotation of the slave surgical instrument tip are not the same.

More generally, as described previously, rotation of the master tool grip about a space-fixed axis in the eye frame results in slave surgical instrument tip rotation about the same space-fixed axis in the camera frame. When the orientation offset is permitted to be large, a rotation of the master tool grip about its pointing direction can result in a circular slave surgical instrument tip motion about the master pointing direction projected onto the slave view frame in the prior system.

Consequently, the prior system would result in unnatural rotation of the slave surgical instrument if the maximum alignment error were increased from the small orientation misalignment to a swooping orientation misalignment. Orientation control module 134 in teleoperation servo controller 160 eliminates the problems with the prior system when there is a swooping orientation misalignment when a following session is initiated.

Orientation control module 134 eliminates the problems associated with the prior systems. First, the criterion for ascertaining whether the misalignment between the master tool grip and slave surgical instrument tip is relaxed. A swooping orientation alignment between master tool grip 230 and slave surgical instrument tip 312T is allowed when entering is enabled.

The larger allowed orientation misalignment means that in most cases, MASTER-SLAVE ALIGNMENT process 250 is run only once and then following is entered. Thus, any frustration that was previously experienced by the surgeon with the prior system due to multiple warnings of misalignment is minimized, if not eliminated.

Second, despite a large initial orientation misalignment, the motion of slave surgical instrument tip 312T intuitively follows the motion of master tool grip 230. There is no unexpected motion associated with rotation of master tool grip 230. Thus, despite the swooping orientation misalignment on entering following, the perceived rotation of master tool grip 230 is the same as the perceived rotation of slave surgical instrument tip 312T. If the rotation of master tool grip 230 is about a body-fixed axis of master tool grip 230, rotation of slave surgical instrument tip 312T is about the same body-fixed axis of slave surgical instrument tip 312T so that the motion of the master and slave is intuitive to the user.

To address the behavior of the prior system when a swooping orientation misalignment is allowed, a "manipulator centric" approach is adopted in orientation control module 134. In the manipulator centric approach, any delta, any relative change, in master tool grip motion is defined with eye frame 330 moving relative to a master tool grip 230 that is fixed in position, i.e., the master frame 340 is a body-fixed frame. Specifically, orientation mRe of the eye frame 330 in the master frame 340 is defined as being equal to the product of relative rotation matrix R2 and stored orientation mRe', i.e., $$mRe = R2 * mRe'$$

Note that it is trivial to obtain orientation mRe of eye frame 330 as viewed in master frame 340 by performing a matrix transpose on the orientation eRm of master frame 340 as viewed in eye frame 330, i.e.:

$$mRe = eRm^T$$

Also, rotation matrices are orthogonal matrices, i.e., $$mRe * eRm = mRe * mRe^T = I$$

where I is the identity matrix.

Thus, $mRe'=eRm'^T$. In this aspect, orientation eRm' from MASTER SLAVE ALIGNMENT process 250 is transposed and orientation mRe' is stored in STORE ORIENTATIONS process 260.

In this aspect, offset matrix Roffset is generated from the stored orientations by multiplying the two stored orientations, e.g., by multiplying the two stored rotation matrices, i.e.:

$$Roffset=cRs'^*mRe'=cRs'^*eRm'^T$$

In this aspect, the desired slave orientation cRs_des in the camera frame is defined as:

$$cRs\_des=Roffset^*eRm \quad (2)$$

Substituting the above definition of rotation offset Roffset in expression (2) gives:

$$cRs\_des=(cRs'^*mRe')^*eRm$$

$$eRm=mRe^T=(R_2^*mRe')^T=mRe'^T{^*}R_2^T \quad (3)$$

Substituting this definition of additional rotation eRm in expression (3) gives $$cRs\_des=(cRs'^*mRe')^*mRe'^T{^*}R_2^T$$

but, $$mRe'^T=eRm'$$

Thus, $$cRs\_des=cRs'^*mRe'^*eRm'^*R_2^T$$

However, as noted above, rotation matrices are orthogonal matrices, i.e., $$mRe'^*eRm'=I$$

Thus, $$cRs\_des=cRs'^*R_2^T \quad (4)$$

Expression (4) shows that desired slave orientation cRs_des in the camera frame is a combination of relative rotation matrix R2 and the base orientation cRs' of the slave surgical instrument tip in the camera frame. Thus, the desired slave orientation is defined relative to base orientation cRs' of the slave surgical instrument tip in the camera frame.

Expression (4) is used to determine desired slave orientation cRs_des in the camera frame in response to a message indicating that master tool grip 230 moved. Orientation control module 134 first computes transposed relative rotation matrix $R2^T$ in master frame 340, e.g., from above relative rotation matrix R2 is defined as $$mRe=R2^*mRe'$$

$$mRe^*mRe'^T=R2^*mRe'^*mRe'^T$$

but $$mRe'^*mRe'^T=I$$

$$R2=mRe^*mRe'^T$$

$$R2^T=(mRe^*mRe'^T)^T$$

$$R2^T=mRe'^*mRe^T$$

$$R2^T=mRe'^*eRm$$

Thus, to compute the transpose of relative rotation matrix R2 for use in expression (6), orientation control module 134 multiplies the master tool tip current rotation matrix eRm and stored orientation mRe'.

To obtain desired slave orientation cRs_des, orientation control module 134 applies the transpose of relative rotation R2 to snapshot slave orientation cRs' in camera frame 310. This process of determining desired slave orientation cRs_des is called "manipulator centric," because the system monitors the delta of the motion of eye frame 330 relative to a fixed in position master tool grip, and replicates that delta on the slave surgical instrument 112 in camera frame 310. This method for generating desired slave orientation cRs_des eliminates the problem with unexpected motion of the slave instrument (FIG. 4D) even though the misalignment between master tool grip 230 and slave surgical instrument tip 312T can be significantly larger than in the prior system.

As an example, assume that the misalignment between master tool grip 230 and slave surgical instrument tip 312T just prior to entering following is the same as described above with respect to FIGS. 4A and 4B. Upon entering following, the surgeon rotates the master tool grip 230, as illustrated in FIG. 5A. The rotation is about body-fixed x-axis Xbm in the Xe-Ye plane. Now, x-axis Xm of the master frame is a body-fixed axis, e.g., rotation is defined with respect to the x-axis that is fixed on the master tool grip. The surgeon is likely to anticipate that the slave surgical instrument tip will rotate about its body-fixed x-axis Xbs in the Xc-Yc plane, i.e., x-axis Xs of the slave frame is fixed and rotation is defined about the x-axis.

Unlike the motion illustrated in FIG. 4D, with this implementation, system 100 effectively describes the relative motion of eye frame 330 in master frame 340, because master frame 340 is considered a body-fixed frame, and preserves the same relationship on the slave side. The rotation about the body-fixed master x-axis Xbm produces a rotation about the body-fixed slave x-axis Xbs as desired and as illustrated in FIG. 5B.

As shown in FIGS. 5A and 5B, desired orientation of the slave surgical instrument tip cRs_des generated by controller 150 preserves a same perceived rotation between master tool grip 230 (FIG. 5A) and slave surgical instrument tip 312T (FIG. 5B) even when there is a swooping orientation misalignment between master tool grip 230 and slave surgical instrument tip 312T. Here, the rotation of the master tool grip 230 is perceived as being in the Xe-Ye plane and the rotation of slave surgical instrument tip 312T is perceived as being in a corresponding Xc-Yc plane so that the perceived motion of master tool grip 230 is the same as the perceived motion of slave surgical instrument tip 312T.

More generally, desired orientation of the slave surgical instrument tip cRs_des generated by controller 150 preserves a same perceived rotation between master tool grip 230 (FIG. 5A) and slave surgical instrument tip 312T. As explained previously, a same perceived rotation means that if the rotation of the master tool grip is perceived as being about a body-fixed axis of the master tool grip, the rotation of the slave surgical instrument is perceived as being about a corresponding body-fixed axis of the slave surgical instrument tip. For example, if the rotation of the master tool grip is perceived as being about the body-fixed x-axis of the master tool grip, the rotation of the slave surgical instrument is perceived as being about a corresponding body-fixed x-axis of the slave surgical instrument tip, or if the rotation of the master tool grip is perceived as being about the body-fixed y-axis of the master tool grip, the rotation of the slave surgical instrument is perceived as being about a corresponding body-fixed y-axis of the slave surgical instrument tip, or if the rotation of the master tool grip is perceived as being about the body-fixed z-axis of the master tool grip, the rotation of the slave surgical instrument is perceived as being about a corresponding body-fixed z-axis of the slave surgical instrument tip.

While a rotation about the x-axis is shown in FIGS. 4A to 4D and 5A and 5B, the same behavior is seen in the prior system and in system 100 for rotation about the y-axis and for rotation about the z-axis. Thus, the description herein applies to each of pitch, yaw, and roll. However, a description and illustration for each of the y-axis and the z-axis is not presented, because it would be redundant with the description with respect to the x-axis. One knowledgeable in the field understands the application to rotations about the y- and z-axes without repeating the description of FIGS. 4A to 4D and 5A and 5B for each of the axes.

Nevertheless, another example is presented. In the prior art system, prior to entering following there is an orientation misalignment between z-axis Zm of master frame 340 in eye frame 330 and z-axis Zs of slave frame 320 in camera frame 310. Specifically, z-axis Zm of master frame 340 is coincident with z-axis Ze of eye frame 330, while z-axis Zs of slave frame 320 is displaced from z-axis Zc of camera frame 310. Z-axis Zs of slave frame 320 lies in the Yc-Zc plane.

As explained above, in the prior system, the axes of master frame 340 and slave frame 320 are spaced fixed. Thus, in the prior system, z-axis Zm of master frame 340 is spaced fixed axis Zsm, and z-axis Zs of slave frame 320 is space fixed z-axis Zss.

Upon entering following, the surgeon rotates the master tool grip, as illustrated in FIG. 5C. The rotation is about space fixed z-axis Zsm in the Ze-Ye plane. Rotation of the master tool grip about space-fixed axis Zsm in the eye frame results in slave surgical instrument tip rotation about the same space-fixed axis Zss in the camera frame. When the orientation offset is permitted to be large, a rotation of the master tool grip about its pointing direction can result in a circular slave surgical instrument tip motion about the master pointing direction projected onto the slave view frame. However, the surgeon is likely to anticipate that the slave surgical instrument tip will rotate about its z-axis Zss in the Zc-Yc plane.

With the swooping orientation misalignment, the prior art system still determines desired slave orientation cRs_des in response to the rotation of the master tool grip as just described. Due to the initial large displacement in orientation, the slave surgical instrument tip does not rotate as expected, because when the relative rotation is applied to the slave surgical instrument tip, the rotation of the slave surgical instrument tip is no longer in the in the Zc-Yc plane. Rather than rotate in the Zc-Yc plane, the slave surgical instrument tip rather rotates along a circular path 501 in camera frame 310. Due to the swooping orientation misalignment, the path of the rotation of slave surgical instrument is displaced from axis Zc as show by path 501.

Thus, in this example, the perceived motion of rotating the master tool grip about a space-fixed axis Zsm of the master tool grip does not result in a perceived motion of the surgical instrument tip rotating about corresponding axis Zc. Rather, as just described, the movement of the slave surgical instrument tip is along a circular path 501. Circular path 501 is in a plane perpendicular to the Zc-Yc plane. Hence, for swooping orientation misalignments in the prior system, the perceived rotation of the master tool grip and the perceived rotation of the slave surgical instrument tip are not the same.

More generally, as described previously, rotation of the master tool grip about a space-fixed axis in the eye frame results in slave surgical instrument tip rotation about the same space-fixed axis in the camera frame. When the orientation offset is permitted to be large, a rotation of the master tool grip about its pointing direction can result in a circular slave surgical instrument tip motion about the master pointing direction projected onto the slave view frame in the prior system.

Unlike the motion illustrated in FIG. 5D, with this implementation, system 100 effectively describes the relative motion of eye frame 330 in master frame 340, because master frame 340 is considered a body-fixed frame, and preserves the same relationship on the slave side. The rotation about the body-fixed master z-axis Zbm produces a rotation about the body-fixed slave z-axis Zbs as desired and as illustrated in FIG. 5F.

As shown in FIGS. 5E and 5F, desired orientation of the slave surgical instrument tip cRs_des generated by controller 150 preserves a same perceived rotation between master tool grip 230 (FIG. 5E) and slave surgical instrument tip 312T (FIG. 5F) even when there is a swooping orientation misalignment between master tool grip 230 and slave surgical instrument tip 312T. Here, the rotation of the master tool grip 230 is perceived as being in the Ze-Ye plane and the rotation of slave surgical instrument tip 312T is perceived as being in a corresponding Zc-Yc plane so that the perceived motion of master tool grip 230 is the same as the perceived motion of slave surgical instrument tip 312T.

Figure 6:
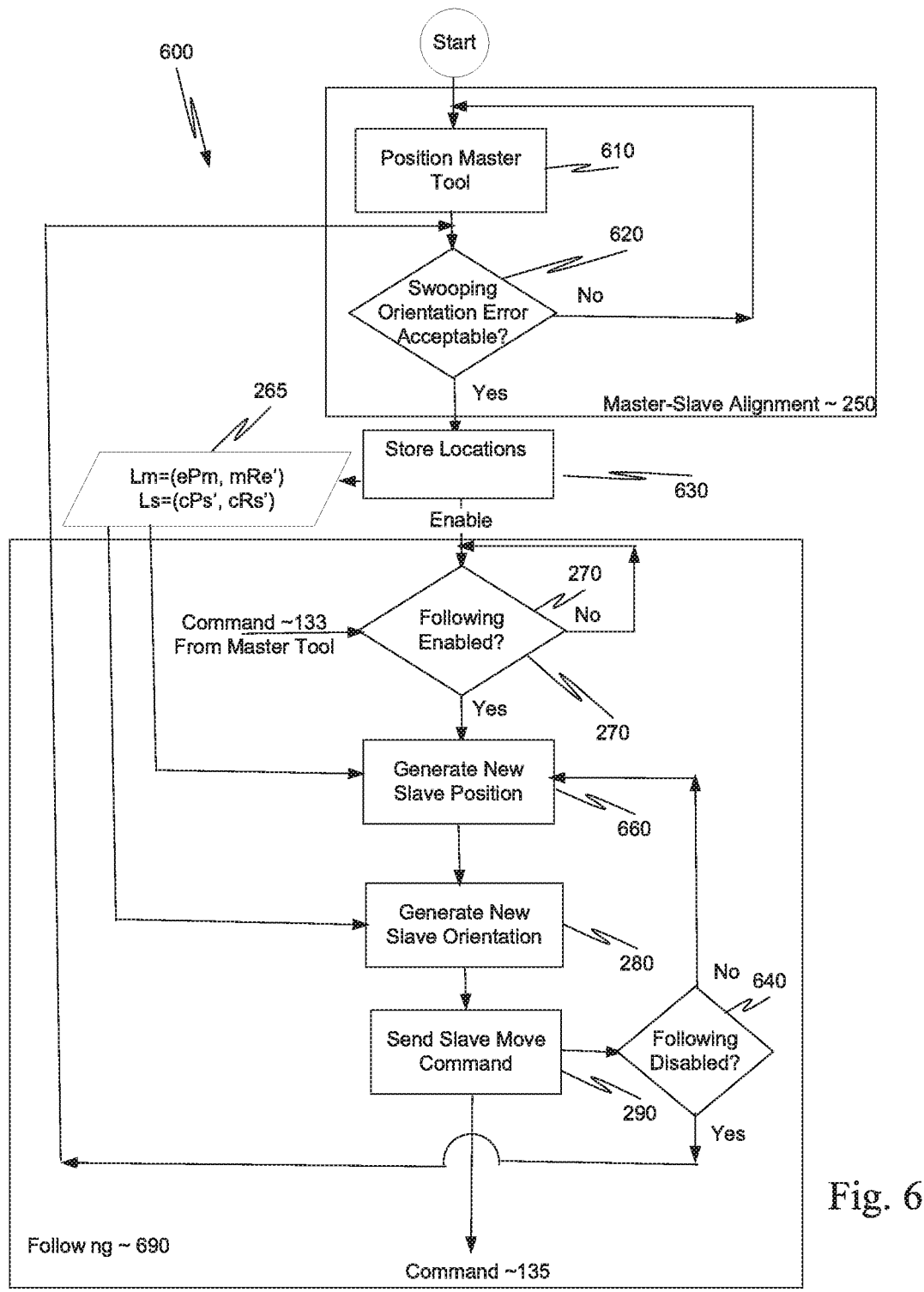
FIG. 6 is a more detailed process flow diagram that illustrates processes implemented by the controller of FIG. 1, in one aspect.

FIG. 6 is a more detailed process flow diagram for one aspect of a process 600 performed by controller 150. For ease of discussion, process 600 is shown as a linear process. This is illustrative only and is not intended to be limiting. In view of the following disclosure, process 600 can be implemented as described below, or alternatively with some or all of the acts being performed in parallel, for example.

When a user, typically a surgeon, first starts a session at surgeon's console 114, MASTER-SLAVE ALIGNMENT process 250 is started. MASTER-SLAVE ALIGNMENT process 250 is implemented by master-salve alignment module 132, which is included in teleoperation servo controller 160. Teleoperation servo controller 160 is included in controller 150. Thus, each of the acts described below with respect to MASTER-SLAVE ALIGNMENT process 250 is performed by controller 150, and so the designation of a teleoperation servo controller is optional.

POSITION MASTER TOOL process 610 of MASTER-SLAVE ALIGNMENT process 250 is equivalent to the process in prior systems. The location (position and orientation) of slave surgical instrument tip 312T is determined in camera frame 310, and then POSITION MASTER TOOL process 610 sends a command to teleoperation servo controller 160 to move master tool grip 230 to a corresponding desired location (position and orientation) in eye frame 330. See the above description in Related Art of how this was done in one aspect.

However, if the surgeon grasps master tool grip 230 too firmly, teleoperation servo controller 160 may not move master tool grip 230 to the desired location. Thus, in this case, there is a misalignment between the location of master tool grip 230 in eye frame 330 and the location of slave surgical instrument tip 312T in camera frame 310. Upon completion of POSITION MASTER TOOL process 610 processing transfers to SWOOPING ORIENTATION ERROR ACCEPTABLE check process 620 in MASTER SLAVE ALIGNMENT process 250.

SWOOPING ORIENTATION ERROR ACCEPTABLE check process 620 determines whether any orientation misalignment between slave surgical instrument tip 312T in camera frame 310 and master tool grip 230 in eye frame 330 is smaller than or equal to a maximum permitted orientation misalignment, i.e., smaller than or equal to a maximum permitted swooping orientation error. Unlike the prior art system that required the maximum orientation misalignment to be equal to or smaller than a few degrees, the limitation on the orientation alignment has been significantly relaxed.

Two factors are used to select the maximum permitted swooping orientation misalignment, in one aspect. The first factor is to make the maximum permitted swooping orientation misalignment large enough that most users of surgical system 100 will not be forced to wait while MASTER-SLAVE ALIGNMENT process 250 is repeated. The second factor is to select the maximum permitted swooping orientation misalignment to avoid confusion between motions about the various axes by the surgeon. For example, if the maximum permitted swooping orientation misalignment were ninety-degrees, yaw motion of the master tool grip would appear as pitch motion of the slave surgical instrument tip, which most likely would be confusing to the surgeon.

The first factor can be determined, for example, by having a number of inexperienced users use surgical system 100, and determine the largest orientation misalignment after MASTER-SLAVE ALIGNMENT process 250 is completed. It has been observed that users with less experience tend to grip master tool grip the hardest, which tends to result in a larger orientation misalignment. Experiments have shown that a maximum permitted swooping orientation misalignment of about fifty degrees does not result in confusion between motions about the various axes.

However, the use of fifty degrees is illustrative only and is not intended to be limiting. In view of this disclosure, one knowledgeable in the field can select a maximum permissible orientation misalignment that is suitable for the users of surgical system 100. For example, in some situation, the maximum permissible orientation might be extended to sixty or more degrees, while in a situation where all the users of surgical system 100 are experienced users, the maximum permitted swooping orientation might be lowered to thirty degrees or less.

In any case, the maximum permitted swooping orientation error is larger than the maximum permitted small orientation misalignment of the prior system. Herein a swooping orientation misalignment is defined as follows. A swooping orientation misalignment is an orientation misalignment such that when the desired slave orientation cRs_des of the slave surgical instrument tip in the camera frames is defined as:

$$cRs\_des = eRm * Roffset\_prior^T$$

Rotation of master tool grip 230 about its pointing direction in eye frame 330 results in slave surgical instrument tip 312T moving in a circle, which is perceptible to the user, about the master pointing direction projected on the slave view frame. When this definition of desired slave orientation cRs_des is used and the maximum permitted swooping orientation misalignment is limited to the small misalignment of the prior art, any circular motion of surgical instrument tip 312T is not perceived by the user.

Thus, a swooping orientation misalignment is larger than the prior maximum permitted small orientation misalignment. This definition is also consistent with the fact the new maximum permitted swooping orientation misalignment is selected to limit the number of iterations of MASTER-SLAVE ALIGNMENT process 250 to obtain a permissible misalignment for entering following. To distinguish the maximum permitted orientation misalignment from the maximum permitted small orientation alignment of the prior system, the maximum permitted orientation misalignment of system 100 is referred to herein as a maximum permitted swooping orientation error.

In one aspect, as described above, SWOOPING ORIENTATION ERROR ACCEPTABLE check process 620 determines whether any orientation misalignment between master tool grip 230 in eye frame 330 and slave surgical instrument in camera frame 310 is smaller than or equal to the maximum permitted larger orientation error. SWOOPING ORIENTATION ERROR ACCEPTABLE check process 620 first determines the orientation misalignment Misalignment Angle as follows.

$$Roffset = CRs' * mRe' = \begin{bmatrix} R11 & R12 & R13 \\ R21 & R22 & R23 \\ R31 & R32 & R33 \end{bmatrix}$$

Misalignment Angle = $acos((R11 + R22 + R33 - 1)/2)$ where acos is the inverse cosine function. If orientation misalignment Misalignment Angle is smaller than or equal to maximum permitted swooping orientation error, SWOOPING ORIENTATION ERROR ACCEPTABLE check process 620 transfers processing to STORE LOCATIONS process 630, and otherwise SWOOPING ORIENTATION ERROR ACCEPTABLE check process 620 returns processing to POSITION MASTER TOOL process 610. Thus, in one aspect, if orientation misalignment Misalignment Angle is smaller than or equal to fifty degrees, SWOOPING ORIENTATION ERROR ACCEPTABLE check process 620 transfers processing to STORE LOCATIONS process 630.

STORE LOCATIONS process 630, sometimes referred to as process 630, includes STORE ORIENTATIONS process 260, in one aspect. In one aspect, STORE LOCATIONS process 630 is implemented by storage module 261.

STORE LOCATIONS process 630, in one aspect, first transposes eRm' to obtain mRe', and then stores location Lm(ePm', mRe') of master tool grip 230 in memory 265 and stores Ls(cPs', cRs') of slave surgical instrument tip 312T in memory 265. Upon completion of STORE LOCATIONS process 630, following is enabled and FOLLOWING process 690 is entered.

FOLLOWING process 690 is implemented by following module 130 which is included in teleoperation servo controller 160, in one aspect. Teleoperation servo controller 160 is included in controller 150. Thus, each of the acts described below with respect to FOLLOWING process 690 is performed by controller 150.

In FOLLOWING process 690, if following is enabled, FOLLOWING ENABLED check process 270 passes each master movement command 133 from the master tool manipulator to GENERATE NEW SLAVE POSITION process 660, and otherwise takes no action.

GENERATE NEW SLAVE POSITION process 660, sometimes referred to as process 660, determines new desired position cPs_des of slave surgical instrument tip 312T in camera frame 310. Master movement command 133 includes a position ePm of master tool grip 230 in eye coordinate frame 330. To determine a relative position change Δ in the position of master tool grip 230, stored position ePm' is retrieved from memory 265 by process 660, and subtracted from position ePm, i.e., $$\Delta = ePm - ePm'$$

where Δ is a three by one matrix. The new desired position cPs_des is:

$$cPs\_des = cPs' + \Delta$$

After determining, new desired position cPs_des, GENERATE NEW SLAVE POSITION process 660 transfers to GENERATE NEW SLAVE ORIENTATION process 280.

GENERATE NEW SLAVE ORIENTATION process 280, sometimes referred to as process 280, determines new desired orientation cRs_des of slave surgical instrument tip 312T in camera frame 310. As described above, $$cRs\_des = cRs'^* R_2^T$$

$$R_2^T = mRe'^* eRm$$

Thus, GENERATE NEW SLAVE ORIENTATION process 280 retrieves stored orientation mRe' and stored orientation cRs', and then multiplies orientations cRs', mRe', and eRm together to generate new desired orientation cRs_des. As explained with respect to FIGS. 5A and 5B, desired orientation of the slave surgical instrument tip cRs_des generated by controller 150 preserves a same perceived rotation between master tool grip 230 and slave surgical instrument tip 312T even when there is a swooping orientation misalignment between master tool grip 230 slave surgical instrument tip 312T. After determining, new desired orientation cRs_des, GENERATE NEW SLAVE ORIENTATION process 280 transfers to SEND SLAVE MOVE COMMAND process 290.

After GENERATE NEW SLAVE ORIENTATION process 280 generates desired orientation cRs_des of the slave surgical instrument tip in the camera frame, SEND SLAVE MOVE COMMAND process 290 sends a slave movement command 135, sometimes referred to as command 135, which includes desired position cPs_des and desired orientation cRs_des to slave surgical instrument manipulator 222. In response to command 135, slave surgical instrument manipulator 222 moves surgical instrument tip 312T of slave surgical instrument 112 to the desired location. In this aspect, after sending slave movement command 135, SEND SLAVE MOVE COMMAND process 290 transfers to FOLLOWING DISABLED check process 640.

If following is disabled by system 100, FOLLOWING DISABLED check process 640 transfers to LARGE ORIENTATION ERROR ACCEPTABLE check process 620, and otherwise returns to GENERATE NEW SLAVE POSITION process 660. FOLLOWING DISABLED check process 640 should not be interpreted as requiring process 690 to poll to determine whether processing has been disabled in every cycle performed by process 690. For example, FOLLOWING process 690 could be allowed until an event handler receives a following disabled event, and then the event handler disables FOLLOWING process 690.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the inventive aspects.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

While the memory is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the methods and/or processes described herein, or in which computer readable code for any one or any for any one or any combination of the methods and/or processes described herein is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a medium configured to store computer readable instructions for any one or any combination of the methods and/or processes described herein, or in which computer readable instructions for any one or any combination of the methods and/or processes described herein, is stored. Tangible computer program products are CD-ROM discs, DVD discs, flash memory, ROM cards, floppy discs, magnetic tapes, computer hard drives and other physical storage mediums.

In view of this disclosure, instructions for any one or any combination of the methods and/or processes described herein can be implemented in a wide variety of computer system configurations using an operating system and computer programming language of interest to the user.

What is claimed is:

1. A system comprising:
a master tool manipulator;
a controller coupled to the master tool manipulator, the controller configured to:
before the system enters following:
determine whether an orientation misalignment between a first orientation of the master tool manipulator in an eye frame before the system enters following and an orientation of a slave instrument tip in a camera frame before the system enters following is less than or equal to a maximum permitted orientation error;
in response to a determination that the orientation misalignment is less than or equal to the maximum permitted orientation error, enable following, and
after the system enters following:
receive a command from the master tool manipulator to move the slave instrument tip, the command indicating a second orientation of the master tool manipulator in the eye frame;
generate a new slave orientation based on the second orientation of the master tool manipulator, the first orientation of the master tool manipulator before the system entered following, and the orientation of the slave instrument tip before the system entered following; and
command the system to orient the slave instrument tip based on the new slave orientation.

2. The system of claim 1, wherein the controller is further configured to, after the system enters following:
determine a relative position change in the master tool manipulator;
determine a new position of the slave instrument tip based on the relative position change in the master tool manipulator; and
command the system to position the slave instrument tip based on the new position of the slave instrument tip.

3. The system of claim 2, wherein the controller is further configured to, in response to the determination that the orientation misalignment is less than or equal to the maximum permitted orientation error:
store a location of the master tool manipulator in the eye frame, and
store a location of the slave instrument tip in the camera frame;
wherein the new position of the slave instrument tip is determined further based on the stored location of the master tool manipulator and the stored location of the slave instrument tip.

4. The system of claim 1, wherein the new slave orientation is generated further based on a relative rotation matrix, the relative rotation matrix representing a relative rotation of the eye frame in a master frame.

5. The system of claim 4, wherein the relative rotation matrix comprises a combination of the second orientation of the master tool manipulator and a stored base orientation of the eye frame in the master frame.

6. The system of claim 1, wherein the controller is further configured to, in response to a determination that the orientation misalignment is greater than the maximum permitted orientation error, command the system to move the master tool manipulator to a desired position and orientation in the eye frame.

7. The system of claim 1, wherein the controller is further configured to, in response to a determination that the orientation misalignment is greater than the maximum permitted orientation error, repeatedly command the system to move the master tool manipulator to a desired position and orientation in the eye frame until the orientation misalignment is less than or equal to the maximum permitted orientation error.

8. The system of claim 1, further comprising a console including a viewer and the master tool manipulator.

9. A method of operating a system comprising a master tool manipulator and a slave instrument manipulator, the method comprising:
before the system enters following:
determining whether an orientation misalignment between a first orientation of the master tool manipulator in an eye frame before the system enters following and an orientation of a slave instrument tip in a camera frame before the system enters following is less than or equal to a maximum permitted orientation error,
in response to determining that the orientation misalignment is less than or equal to the maximum permitted orientation error, enabling following; and
after the system enters following:
receiving a command from the master tool manipulator to move the slave instrument tip, the command indicating a second orientation of the master tool manipulator in the eye frame,
generating a new slave orientation based on the second orientation of the master tool manipulator, the first orientation of the master tool manipulator before the system entered following, and the orientation of the slave instrument tip before the system entered following, and
using the slave instrument manipulator to orient the slave instrument tip based on the new slave orientation.

10. The method of claim 9, further comprising:
after the system enters following:
determining a relative position change in the master tool manipulator;
determining a new position of the slave instrument tip based on the relative position change in the master tool manipulator; and
using the slave instrument manipulator to position the slave instrument tip based on the new position of the slave instrument tip.

11. The method of claim 10, further comprising:
in response to the determining that the orientation misalignment is less than or equal to the maximum permitted orientation error:
storing a location of the master tool manipulator in the eye frame, and
storing a location of the slave instrument tip in the camera frame;
wherein the new position of the slave instrument tip is determined further based on the stored location of the master tool manipulator and the stored location of the slave instrument tip.

12. The method of claim 9, wherein the new slave orientation is generated further based on a relative rotation matrix, the relative rotation matrix representing a relative rotation of the eye frame in a master frame.

13. The method of claim 12, wherein the relative rotation matrix comprises a combination of the second orientation of the master tool manipulator and a stored base orientation of the eye frame in the master frame.

14. The method of claim 9, further comprising:
in response to determining that the orientation misalignment is greater than the maximum permitted orientation error, sending a command to move the master tool manipulator to a desired position and orientation in the eye frame.

15. The method of claim 9, further comprising:
in response to determining that the orientation misalignment is greater than the maximum permitted orientation error, repeatedly sending a command to move the master tool manipulator to a desired position and orientation in the eye frame until the orientation misalignment is less than or equal to the maximum permitted orientation error.

16. A non-transitory computer-readable medium comprising a plurality of machine-readable instructions which when executed by one or more processors associated with a robotic system comprising a master tool manipulator are adapted to cause the one or more processors to perform a method comprising:
before the robotic system enters following:
determining whether an orientation misalignment between a first orientation of the master tool manipulator in an eye frame before the robotic system enters following and an orientation of a slave instrument tip in a camera frame before the robotic system enters following is less than or equal to a maximum permitted orientation error, and
in response to determining that the orientation misalignment is less than or equal to the maximum permitted orientation error, enabling following; and
after the robotic system enters following:
receiving a command from the master tool manipulator to move the slave instrument tip, the command indicating a second orientation of the master tool manipulator in the eye frame,
generating a new slave orientation based on the second orientation of the master tool manipulator, the first orientation of the master tool manipulator before the robotic system entered following, and the orientation of the slave instrument tip before the robotic system entered following, and
commanding the robotic system to orient the slave instrument tip based on the new slave orientation.

17. The non-transitory computer-readable medium of claim 16, wherein the method further comprises, after the system enters following:
determining a relative position change in the master tool manipulator;
determining a new position of the slave instrument tip based on the relative position change in the master tool manipulator; and
commanding the robotic system to position the slave instrument tip based on the new position of the slave instrument tip.

18. The non-transitory computer-readable medium of claim 17, wherein the method further comprises:
in response to the determining that the orientation misalignment is less than or equal to the maximum permitted orientation error:
storing a location of the master tool manipulator in the eye frame, and
storing a location of the slave instrument tip in the camera frame;
wherein the new position of the slave instrument tip is determined further based on the stored location of the master tool manipulator and the stored location of the slave instrument tip.

19. The non-transitory computer-readable medium of claim 16, wherein:
the new slave orientation of the slave instrument tip is generated further based on a relative rotation matrix, the relative rotation matrix representing a relative rotation of the eye frame in a master frame; and
the relative rotation matrix comprises a combination of the second orientation of the master tool manipulator and a stored base orientation of the eye frame in the master frame.

20. The non-transitory computer-readable medium of claim 16, wherein the method further comprises:
in response to determining that the orientation misalignment is greater than the maximum permitted orientation error, sending a command to move the master tool manipulator to a desired position and orientation in the eye frame.

* * * * *

UNITED STATES PATENT AND TRADEMARK OFFICE
CERTIFICATE OF CORRECTION

PATENT NO. : 11,083,532 B2
APPLICATION NO. : 16/693119
DATED : August 10, 2021
INVENTOR(S) : Hsien-Hsin Liao Page 1 of 1

It is certified that error appears in the above-identified patent and that said Letters Patent is hereby corrected as shown below:

On the Title Page

(63) Related U.S. Application Data:
Please delete "Continuation of application No. 15/564,160, filed as application No. PCT/US2016/036863 on Jun. 10, 2016, now Pat. No. 10,524,871." and insert --Continuation of application No. 15/564,160, filed on Oct. 3, 2017, now Pat. No. 10,524,871, which is a 371 of application No. PCT/US2016/036863, filed on Jun. 10, 2016.--.

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*